United States Patent [19]

Leigh et al.

[11] Patent Number: 5,777,115

[45] Date of Patent: Jul. 7, 1998

[54] ACETAL-AND KETAL-SUBSTITUTED PYRIMIDINE COMPOUNDS

[75] Inventors: Alistair Leigh; Gail Underiner, both of Brier, Wash.

[73] Assignee: Cell Therapeutics, Inc., Seattle, Wash.

[21] Appl. No.: 193,331

[22] Filed: Feb. 7, 1994

Related U.S. Application Data

[63] Continuation-in-part of Ser. No. 4,353, Jan. 14, 1993, abandoned.

[51] Int. Cl.[6] .................. C07D 239/26; A61K 31/505
[52] U.S. Cl. ............... 544/242; 544/267; 514/269; 514/270; 514/256
[58] Field of Search .................. 544/267, 242; 546/242, 243; 514/256, 269, 270

[56] References Cited

U.S. PATENT DOCUMENTS

| | | | |
|---|---|---|---|
| 3,422,107 | 1/1969 | Mohler et al. | 260/340 |
| 3,737,433 | 6/1973 | Mohler et al. | 260/340 |
| 3,772,337 | 11/1973 | Hamb et al. | 260/340.9 |
| 4,515,795 | 5/1985 | Hinze et al. | 544/267 |
| 4,565,817 | 1/1986 | Karbonits et al. | 544/138 |
| 4,576,947 | 3/1986 | Hinze et al. | 544/267 |
| 4,636,507 | 1/1987 | Kreutzer et al. | 544/267 |
| 4,833,146 | 5/1989 | Gebert et al. | 514/263 |
| 4,965,271 | 10/1990 | Mandell et al. | 514/263 |
| 5,039,666 | 8/1991 | Novick et al. | 514/39 |
| 5,096,906 | 3/1992 | Mandell et al. | 514/263 |
| 5,102,876 | 4/1992 | Caufield et al. | 540/456 |
| 5,118,500 | 6/1992 | Hänel et al. | 514/263 |
| 5,120,725 | 6/1992 | Kao et al. | 514/183 |
| 5,141,943 | 8/1992 | Naguib et al. | 514/270 |
| 5,175,291 | 12/1992 | Kufner-Muhl | 544/267 |

FOREIGN PATENT DOCUMENTS

| | | |
|---|---|---|
| 8096087 | 12/1981 | Japan. |
| 58-096-087 | 6/1983 | Japan. |
| 1201997 | 8/1970 | United Kingdom. |

OTHER PUBLICATIONS

Chemical Abstracts, vol. 94: 127364t, p. 127365, 1981.
Bianco et al., Blood, 76:Supplement 1 (522), p. 133a, "Pentoxifylline (PTX) and GM-CSF Decrease Tumor Necrosis Factor-Alpha (TNF-α) Levels in Patients Undergoing Allogeneic Bone Marrow Transplantation (BMT)," 1991.

Bianco et al., Blood, "Phase I–II Trial of Pentoxifylline for Prevention of Transplant-Related Toxicities Following Bone Marrow Transplantation," 78:1205, 1991.

Davis et al., Applied Environment Microbial., 48:2, pp. 327–331, "Microbial Models of Mammalian Metabolism: Microbial Reduction and Oxidation of Pentoxifylline," Aug. 1984.

Singer et al., Bone Marrow Transplantation, 10:19, pp. 19–25, "Effect of Methylxanthine Derivatives on T Cell Activation," 1992.

Primary Examiner—Mukund J. Shah
Assistant Examiner—Pavanaram K. Sripada
Attorney, Agent, or Firm—Foley & Lardner

[57] ABSTRACT

Acetal-and ketal-substituted compounds and pharmaceutical compositions thereof have the following formula:

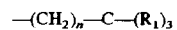

CORE MOIETY—$(R)_j$ including resolved enantiomers and/or diastereomers, hydrates, salts, solvates and mixtures thereof. j is an integer from one to three, the core moiety is non-cyclic or cyclic a monocyclic moiety having at least one nitrogen atom within the ring and R may be selected from among hydrogen, halogen, hydroxyl, amino, substituted or unsubstituted alkyl $C_{(1-6)}$, alkenyl $C_{(2-6)}$, cyclic or heterocyclic groups, and groups having a structure prescribed by formula I. At least one R has the formula I:

$$-(CH_2)_n-C-(R_1)_3 \qquad \text{I}$$

wherein n is an integer from three to twenty; $R_1$ is selected from among hydrogen; halogen; hydroxide; substituted or unsubstituted $C_{(1-6)}$ alkyl, $C_{(1-6)}$ alkoxy, $C_{2-6}$ alkenyl, cyclic or heterocyclic group; —$OR_2$, $R_2$ being hydrogen or a substituted or unsubstituted $C_{(1-6)}$ alkyl, $C_{(2-6)}$ alkenyl, cyclic or heterocyclic group; —$(CH_2)_p$—$C(R_3)_3$ (wherein p is zero or an integer from one to ten, $R_3$ is hydrogen, halogen, hydroxide, substituted or unsubstituted $C_{(1-6)}$ alkyl, $C_{(1-6)}$ alkoxy, $C_{(2-6)}$ alkenyl, cyclic or heterocyclic group, or —$OR_2$, $R_2$ being defined above). The inventive compounds are useful in a large variety of therapeutic indications for treating or preventing disease mediated by intracellular signaling through specific intracellular signaling pathways.

13 Claims, 5 Drawing Sheets

ACETAL-AND KETAL-SUBSTITUTED PYRIMIDINE COMPOUNDS

CROSS REFERENCE TO RELATED APPLICATION

This is a continuation-in-part application of U.S. application Ser. No. 08/004,353, filed Jan. 14, 1993 now abandoned.

TECHNICAL FIELD OF THE INVENTION

The invention relates to a class of acetal-and ketal-substituted therapeutic compounds that are effective agents to modulate cellular responses to stimuli. More specifically, the inventive compounds have at least one acetal-or ketal-substituted side chain bonded to a core moiety. The inventive compounds are useful in a large variety of therapeutic indications for treating or preventing disease mediated by intracellular signaling through specific intracellular signaling pathways.

BACKGROUND OF THE INVENTION

Pentoxifylline (1-(5-oxohexyl)-3,7-dimethylxanthine), abbreviated PTX, is a xanthine derivative which has seen widespread medical use for the increase of blood flow. PTX is disclosed in U.S. Pat. Nos. 3,422,107 and 3,737,433, both to Mohler et al. Metabolites of PTX were summarized in Davis et al., *Applied Environment Microbiol.* 48:327, 1984. A metabolite of PTX is 1-(5-hydroxyhexyl)-3,7-dimethylxanthine, designated M1. M1 was also disclosed as increasing cerebral blood flow in U.S. Pat. Nos. 4,515,795 and 4,576,947 to Hinze et al. In addition, U.S. Pat. Nos. 4,833,146 and 5,039,666 to Gebert et al. and Novick, Jr., respectively, disclose use of tertiary alcohol analogs of xanthine for enhancing cerebral blood flow.

Furthermore, U.S. Pat. No. 4,636,507 to Kreutzer et al. describes an ability of PTX and M1, to stimulate chemotaxis in polymorphonuclear leukocytes in response to a stimulator of chemotaxis. PTX and related tertiary alcohol substituted xanthines inhibit activity of certain cytokines to affect chemotaxis (U.S. Pat. Nos. 4,965,271 and 5,096,906 to Mandell et al.). Administration of PTX and GM-CSF decrease tumor necrosis factor (TNF) levels in patients undergoing allogeneic bone marrow transplant (Bianco et al., *Blood* 76: Supplement 1 (522A), 1990). Reduction in assayable levels of TNF was accompanied by reduction in bone marrow transplant-related complications. However, in normal volunteers, TNF levels were higher among PTX recipients. Therefore, elevated levels of TNF are not the primary cause of such complications.

Therefore, there is a need in the art to discover effective therapeutic compounds that are safe and effective for human or animal administration and can maintain cellular homeostasis in the face of a variety of inflammatory stimuli. The present invention was made in a process of looking for such compounds.

SUMMARY OF THE INVENTION

The inventive compounds, the genus of which is described herein, are useful in a large variety of therapeutic indications for treating or preventing disease mediated by intracellular signaling through specific intracellular signaling pathways. The invention provides a genus of compounds having at least one acetal-or ketal-containing side chain, preferably cyclic or heterocyclic compounds. The inventive compounds and pharmaceutical compositions thereof have the formula:

CORE MOIETY—(R)$_j$ including resolved enantiomers and/or diastereomers, hydrates, salts, solvates and mixtures thereof, wherein j is an integer from one to three, the core moiety is non-cyclic or cyclic and R may be selected from among: hydrogen, halogen (preferably bromine, chlorine, fluorine and iodine), hydroxyl, amino, substituted or unsubstituted $C_{(1-6)}$ alkyl, $C_{(2-6)}$ alkenyl, cyclic or heterocyclic groups, and groups having a structure prescribed by formula I, below.

Preferred R substituents having a structure other than prescribed by formula I below include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or hydrogen.

In the inventive compounds, at least one R has the formula I:

—(CH$_2$)$_n$—C—(R$_1$)$_3$,         I wherein n is an integer from three to twenty; R$_1$ is selected from among: hydrogen; halogen; hydroxide; substituted or unsubstituted $C_{(1-6)}$ alkyl, $C_{(1-6)}$ alkoxy, $C_{(2-6)}$ alkenyl, cyclic or heterocyclic group; —OR$_2$, R$_2$ being hydrogen or a substituted or unsubstituted $C_{(1-6)}$ alkyl, $C_{(2-6)}$ alkenyl, cyclic or heterocyclic group; —(CH$_2$)$_p$—C(R$_3$)$_3$ (wherein p is zero or an integer from one to ten, R$_3$ is hydrogen, halogen, hydroxide, substituted or unsubstituted $C_{(1-6)}$ alkyl, $C_{(1-6)}$ alkoxy, $C_{(2-6)}$ alkenyl, cyclic or heterocyclic group, or —OR$_2$, R$_2$ being defined above); and at least two R$_1$ or two R$_3$ are —OR$_2$ or jointly form —(CH$_2$)$_s$—O—C(R$_4$)$_2$—O—(CH$_2$)$_t$— (wherein s and t are independently zero, one or two, a sum of s and t is less than three, and R$_4$ is hydrogen, halogen or substituted or unsubstituted $C_{(1-6)}$ alkyl, $C_{(2-6)}$ alkenyl, cyclic or heterocyclic group). In the inventive compounds, no more than one R$_2$, corresponding to the at least two R$_1$ or two R$_3$ which are —OR$_2$, is hydrogen and a third R$_1$ or third R$_3$, bonded to the same —C as both the at least two R$_1$ or two R$_3$, is other than —OR$_2$.

Optionally, two terminal R$_2$ of —C(OR$_2$)$_2$ may join to form a heterocyclic group having from four to seven ring atoms, the O of each —OR$_2$ being a hetero atom of the heterocycle. Also, (CH$_2$)n and/or (CH$_2$)$_p$ optionally may have one or two unsaturated bonds (preferably in a cis configuration) or be interrupted by at least one oxygen atom.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

A cyclic core may be at least one five-to seven-member non-heterocyclic ring or a heterocycle. The at least one five-to seven-membered non-heterocyclic ring may preferably have from one to three, five-to six-membered ring structures in a predominantly planar configuration. For example, the core moiety may be selected from the group consisting of substituted or unsubstituted benzene; biphenyl; cyclohexane; cyclohexanedione; cyclopentanedione; napthlalene; phenol; salicylic acid and derivatives thereof; stilbene or tricyclododecane.

Although other heterocyclic cores are within the scope of the invention, the following cores are representative heterocyclic cores: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinolone; recorsinol; succinimide; theobromine; thymine; triazine; uric acid; uracil; vitamins A, E or K; or xanthine.

Preferably, R is bonded to a nitrogen of the core moiety, most preferably the core moiety is xanthine and R of formula I is bonded to an $N_1$ xanthine nitrogen and $N_3$ and $N_7$ xanthine nitrogens are independently substituted by a member selected from the group consisting of hydrogen, methyl, fluoro, chloro and amino. Representative, preferred inventive compounds are compounds of formula II:

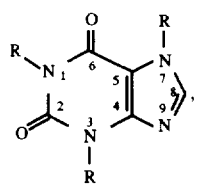

wherein R is defined above.

The present invention further provides pharmaceutical compositions suitable for normal routes of therapeutic administration, providing effective compound dosages. The inventive pharmaceutical compositions comprise inventive compound and a pharmaceutically acceptable excipient or carrier, formulated for, e.g., parenteral, oral, topical and other known methods of pharmaceutical administration.

The invention includes a method for treating an individual having a variety of diseases. The disease is characterized by or can be treated by inhibiting an immune response or a cellular response to external or in situ primary stimuli, the cellular response being mediated through a specific phospholipid-based second messenger pathway described herein. The second messenger pathway is activated in response to various noxious, proinflammatory or proliferative stimuli characteristic of a variety of disease states. More specifically, the invention includes methods for treating or preventing clinical symptoms of various disease states or reducing toxicity of other treatments by inhibiting cellular signaling through a second messenger pathway involving signaling through a non-arachidonyl phosphatidic acid intermediate.

A disease state or treatment-induced toxicity are selected from the group consisting of: tumor progression involving tumor stimulation of blood supply (angiogenesis) by production of fibroblast growth factor (FGF), vascular endothelial growth factor (VEGF) or platelet-derived growth factor (PDGF); tumor invasion and formation of metastases through adhesion molecule binding, expressed by vascular endothelial cells (VCAM and ICAM); tissue invasion through tumor metalloprotease production such as MMP-9; autoimmune diseases caused by dysregulation of the T cell or B cell immune systems, treatable by suppression of the T cell or B cell responses; acute allergic reactions including, but not limited to, asthma and chronic inflammatory diseases, mediated by pro-inflammatory cytokines including tumor necrosis factor (TNF) and IL-1; rheumatoid arthritis, osteoarthritis, multiple sclerosis or insulin dependent diabetes mellitus (IDDM), associated with enhanced localization of inflammatory cells and release of inflammatory cytokines and metalloproteases; smooth muscle cell, endothelial cell, fibroblast and other cell type proliferation in response to growth factors, such as PDGF-AA, BB, FGF, EGF, etc. (i.e., atherosclerosis, restenosis, stroke, and coronary artery disease); activation of human immunodeficiency virus infection (AIDS and AIDS related complex); HIV-associated dementia; kidney mesengial cell proliferation in response to IL-1, MIP-1α, PDGF or FGF; kidney glomerular or tubular toxicity in response to cyclosporin A or amphotericin B treatment; organ toxicity (e.g., gastrointestinal or pulmonary epithelial) in response to a cytotoxic therapy (e.g., cytotoxic drug or radiation); effects of non-alkylating anti-tumor agents; inflammation, particularly in response to inflammatory stimuli (e.g., TNF, IL-1 and the like), characterized by production of metalloproteases or allergies due to degranulation of mast cells and basophils in response to IgE or RANTES; bone diseases caused by overproduction of osteoclast-activating factor (OAF) by osteoclasts; central nervous system diseases resulting from over-stimulation by proinflammatory neurotransmitters such as, acetylcholine, serotonin, leuenkephalin or glutamate; acute inflammatory diseases such as septic shock and adult respiratory distress syndrome; multi-organ dysfunction associated with inflammatory cytokine cascade and combinations thereof.

In many cell types, signaling is dependent upon generation of a broad variety of non-arachidonyl PA species, some of which are generated from lyso-PA by the enzyme lyso-PA acyl transferase (LPAAT). Generation of each of these PA species (the predominant forms being: 1-acyl, and 1-alkyl, 2-linoleoyl PA compounds, generated by LPAAT) serves to effect both proliferative and/or inflammatory signaling in the diseases discussed and cell signaling systems described above.

The inventive compounds are of particular significance for inhibiting IL-2-induced, proliferative response. IL-2 signaling inhibition is potentially useful in the treatment of numerous disease states involving T-cell activation and hyperproliferation. Exemplary, important autoimmune diseases are lupus, scleroderma, rheumatoid arthritis, multiple sclerosis, glomerula nephritis, insulin dependent diabetes mellitus (IDDM), as well as potential malignancies, including but not limited to, chronic myelogenous leukemia as well as others.

BRIEF DESCRIPTION OF THE DRAWINGS

FIG. 6 shows an analysis of mean fluorescence intensity of cells analyzed by flow cytometry for compounds nos. 1567 and 1573 at indicated drug concentrations.

DETAILED DESCRIPTION OF PREFERRED EMBODIMENTS

Figure 1:
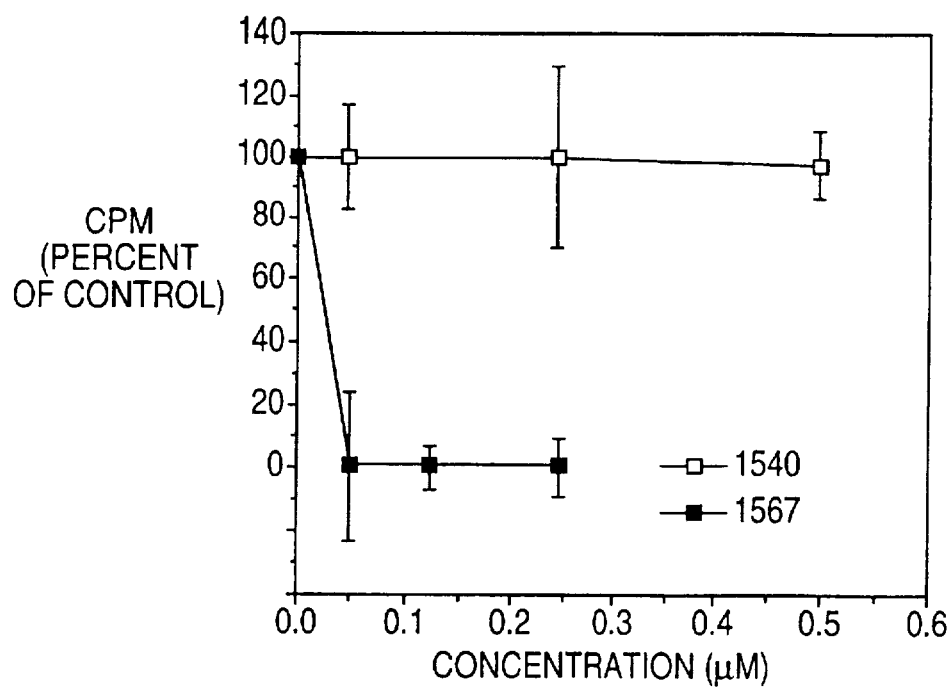
FIG. 1 shows a mixed lymphocyte reaction of comparative compound no. 1540 and inventive compound no. 1567 (see below for inventive compound chemical name and structure). Inventive compound no. 1567, but not comparative compound no. 1540, showed activity in this immune modulating activity assay procedure.

The invention provides a genus of compounds which can control cellular behavior by a particular phase of a secondary messenger pathway system (Bursten et al., *J. Biol. Chem.* 266:20732, 1991). The second messengers are lipids or phospholipids and use the following abbreviations:

PE=phosphatidyl ethanolamine

LPE=lysophosphoethanolamine

PA=phosphatidic acid

LPA=lysophosphatidic acid

DAG=diacylglycerol

LPLD=lysophospholipase-D

LPAAT=lysophosphatidic acid acyl transferase

PAPH=phosphatidic acid phosphohydrolase

PLA2=phospholipase A2.

PLD=phospholipase D

PAA=phosphoarachidonic acid

PC=phosphatidyl choline

"remodeled" PA, cyclic pathway=PAA, LPA, PA and DAG intermediates substituted with 1-saturated, 2-linoleoyl or 1,2-dioleoyl, dioleoyl/1,2-sn-dilinoleoyl at the indicated sn-1 and sn-2 positions.

"Classical PI Pathway" =PI, DAG, PA intermediates substituted with 1-stearoyl, 2-arachidonoyl fatty acyl side chains.

"PLD-generated PA" =PE, PC, LPA, PA and DAG intermediates substituted with, e.g., 1,2-sn-dioleoyl-, 1-alkyl, 2-linoleoyl-, and 1-alkyl, 2-docosahexaenoyl-side chains.

Lysophosphatidic acid transferase (LPAAT) effects the synthesis of phosphatidic acid (PA) from lysophosphatidic acid (LPA) by incorporation of an acyl group from acyl CoA. Hydrolysis of the phosphate moiety by PA phosphohydrolase (PAPH) results in the formation of DAG. These aspects of the pathway appear to be activated immediately (within a minute) upon stimulation by a primary stimulus (e.g., a cytokine such as IL-1, IL-2 or TNF) acting at a receptor on a cellular surface. An immediate detectable effect is an elevation of levels of PA and DAG. Administration of the compounds of the invention reverse this elevation.

The compounds and pharmaceutical compositions of the invention include inhibitors of subspecies of LPAAT and PAPH enzymes with substrate specificity for intermediates with 1,2-diunsaturated and 1-alkyl, 2-unsaturated subspecies. One representative example of such an inhibitor (although not within the genus of inventive compounds) is PTX. PTX blocks PAPH in a specific activation pathway that does not involve PI but rather derives from a PA that is largely composed of 1,2-diunsaturated and 1-alkyl, 2-unsaturated subspecies. This was shown, for example, by the demonstration that human mesangial cells stimulated with TNF produce DAG from PI and regenerate PI in the absence and the presence of PTX. In the latter system there is no evidence to suggest that PA or DAG are derived from sources other than PI. It should be emphasized that the compounds of the invention affect that subset of PAPH and LPAAT that relates to substrates with unsaturated fatty acids other than arachidonate in the sn-2 position, not the housekeeping forms of these enzymes that serve the PI pathway.

Each membrane phospholipid subclass (e.g., PA, PI, PE, PC and PS) reaches a stable content of characteristic fatty acyl side chains due to cyclic remodeling of the plasma membrane as well as turnover for each subclass. PA is often stable, but present in relatively small quantities. PA in resting cells consists mostly of saturated acyl chains, usually consisting of myristate, stearate and palmitate. In resting cells, PC's acyl side chains consist mostly of acyl palmitate in the sn-1 position and oleate in the sn-2 position. PE and PI are predominantly composed of sn-1 stearate and sn-2 arachidonate.

Due to this characteristic content of acyl groups in the sn-1 and sn-2 positions, the origin of any PA species may be deduced from the chemical nature of its acyl groups in the sn-1 and sn-2 positions. For example, if PA is derived from PC through action of the enzyme PLD, the PA will contain the characteristic acyl side chains of PC substrate passed through the second messenger pathway. Further, the origin of any 1,2 sn-substrate species may be differentiated as to its origin. It is important to know whether or not each phospholipid species passes through a PA form prior to hydrolysis to DAG. The lyso-PA that is converted to PA and then to DAG may be shown. The complexities of this second messenger pathway can be sorted by suitable analyses using fatty acyl side chain chemistry (e.g., by thin layer chromatography, gas-liquid chromatography, or high pressure liquid chromatography) of intermediates in cells at various time points after stimulation of the second messenger pathway.

In certain meseachymal cells, such as neutrophils and rat or human mesangial cells, several signaling pathways may be activated in tandem, simultaneously or both. For example, in neutrophils, F-Met-Leu-Phe-stimulates formation of PA through the action of PLD, followed in time by formation of DAG through PAPH action. Several minutes later, DAG is generated from PI through the classical phosphoinositide pathway. In many cells, DAG is derived from both PA that is remodeled through a cycle whereby PA is sn-2 hydrolyzed by PLA2, followed by sn-2 transacylation by LPAAT and PA that is generated in a PLD-pathway from either PE or PC or both substrates by PLD.

The present second messenger pathway involves substrates with unsaturated fatty acids in the sn-2 position other than arachidonate and those sub-species of PAPH and LPAAT that are not involved in normal cellular housekeeping functions that are part of the classical PI pathway. The PAPH and LPAAT enzymes involved in this specific second messenger pathway are exquisitely stereo-specific for different acyl side chains and isomeric forms of substrates. Therefore, the inventive compounds may preferably be substantially enantiomerically pure.

PTX (in vitro) blocks formation of remodeled PA through the PA/DAG pathway at high PTX concentrations (greater than those that could be achieved in patients without dose-limiting side effects) by blocking formation of PA subspecies at LPAAT. Even in the presence of PTX, cells continue to form PA through the action of PLD, and DAG is also formed through the action of phospholipase C on PC and PI. The latter pathway are not inhibited by the inventive compounds or PTX. In PTX-treated cells, DAG derived from remodeled and PLA-generated PA is diminished (e.g., 1,2-sn-dioleoyl DAG, 1-alkyl, 2-linoleoyl DAG and 1-alkyl, 2-docosahexaneolyl DAG). Therefore, the inventive compounds and PTX inhibit the formation of only a certain species of PA and DAG by selectively inhibiting a specific second messenger pathway that is only activated in cells by noxious stimuli, but is not used to signal normal cellular housekeeping functions.

Therapeutic Uses of the Inventive Compounds

The specific activation inhibition of the second messenger pathway, as described above and activated primarily by various noxious stimuli, suggests that the inventive compounds are useful in treating a wide variety of clinical indications, mediated at the cellular level by a common mechanism of action. Moreover, in vitro and in vivo data presented herein provides predictive data that a wide variety of clinical indications, having similar effects on the specific second messenger pathway (activated by noxious stimuli and mediated through, for example, inflammatory cytokines), may be treated by the inventive compounds, which specifically inhibit the pathway. In fact, the mechanism of action for the inventive compounds explains why these compounds have multifarious clinical indications.

Activation of the second messenger pathway is a major mediator of response to noxious stimuli and results in cellular signals that lead to, for example, acute and chronic inflammation, immune response and cancer cell growth. Although the inventive compounds may desirably inhibit other noxious stimuli not discussed, they most effectively mediate the above conditions. Signals mediated by the present second messenger pathway include, for example, those cellular responses of LPS directly; T cell activation by antigen; B cell activation by antigen, cellular responses to IL-1, mediated through the IL-1 Type I receptor (but not the IL-1 Type II receptor), and TNF (Type I receptor), growth stimulated by transformations including, but not limited to, activated oncogenes (e.g., ras, abl, her 2-neu and the like), smooth muscle cell proliferation stimulated by PDGF, b-FGF and IL-1; T cell and B cell growth stimulation by IL-2, IL-4 or IL-7 and IL-4 or IL-6, respectively; and more generally, T cell receptor signaling.

In vitro, the inventive compounds: (1) block IL-1 signal transduction through the Type 1 receptor as shown, for example, by preventing IL-1 and IL-1 plus PDGF (platelet derived growth factor) induction of proliferation of smooth muscle, endothelial and kidney mesengial cells; (2) suppress up-regulation of adhesion molecules as shown, for example, by blocking VCAM in endothelial cells; (3) inhibit TNF, LPS and IL-1 induced metalloproteases (an inflammation model); (4) block LPS, TNF or IL-1 induced metalloprotease and secondary cytokine production (for prevention and treatment of septic shock); (5) suppress T cell and B cell activation by antigen, for example, IL-2 and IL-4; (6) inhibit mast cell activation by IgE; (7) are cytotoxic for transformed cells and tumor cell lines, yet not for normal cells; and (8) block signaling by IL-2, IL-4, IL-6 and IL-7 on T and B cells.

The foregoing in vitro effects give rise to the following in vivo biological effects, including, but not limited to: protection and treatment of endotoxic shock and sepsis induced by gram positive or gram negative bacteria; inhibition of tumor cell growth; synergistic immunosuppression, active in autoimmune diseases and in suppressing allograft reactions; and stimulation of hair grow through reversal of an apoptotic process. The inventive compounds are most potent when used to prevent and treat septic shock, treat acute and chronic inflammatory disease, treat or prevent an autoimmune disease and stimulate hair growth (when applied topically).

The inventive compounds also are useful as an adjuvant to inhibit toxic side effects of drugs whose side effects are mediated through the present second messenger pathway.

Metalloproteases mediate tissue damage such as glomerular diseases of the kidney, joint destruction in arthritis, and lung destruction in emphysema, and play a role in tumor metastases. Three examples of metalloproteases include a 92 kD type V gelatinase induced by TNF, IL-1 and PDGF plus bFGF, a 72 kD type IV collagenase that is usually constitutive and induced by TNF or IL-1, and a stromelysin/PUMP-1 induced by TNF and IL-1. The inventive compounds can inhibit TNF or IL-1 induction of the 92 kD type V gelatinase inducable metalloprotease. Moreover, the inventive compounds can reduce PUMP-1 activity induced by 100 U/ml of IL-1. Accordingly, the inventive compounds prevent induction of certain metalloproteases induced by IL-1 or TNF and are not involved with constitutively produced proteases (e.g., 72 kD type IV collagenase) involved in normal tissue remodeling.

The inventive compounds inhibit signal transduction mediated through the Type I IL-1 receptor, and are therefore considered as IL-1 antagonists. A recent review article entitled "The Role of Interleukin-1 in Disease" (Dinarello et al., N. Engl. J. Med. 328, 106, Jan. 14, 1993) described the role of IL-1 as "an important rapid and direct determinant of disease . . . In septic shock, for example, IL-1 acts directly on the blood vessels to induce vasodilatation through the rapid production of platelet activating factor and nitric oxide, whereas in autoimmune disease it acts by stimulating other cells to produce cytokines or enzymes that then act on the target tissue. " The article describes a group of diseases that are mediated by IL-1 , including sepsis syndrome, rheumatoid arthritis, inflammatory bowel disease, acute and myelogenous leukemia, insulin-dependent diabetes mellitus, atherosclerosis and other diseases including transplant rejection, graft versus host disease (GVHD), psoriasis, asthma, osteoporosis, periodontal disease, autoimmune thyroiditis, alcoholic hepatitis, premature labor secondary to uterine infection and even sleep disorders. Since the inventive compounds inhibit cellular signaling through the IL-1 Type I receptor and are IL-1 antagonists, the inventive compounds are useful for treating all of the above-mentioned diseases.

For example, for sepsis syndrome, the mechanism of IL-1-induced shock appears to be the ability of IL-1 to increase the plasma concentrations of small mediator molecules such as platelet activating factor, prostaglandin and nitric oxide. These substances are potent vasodilators and induce shock in laboratory animals. Blocking the action of IL-1 prevents the synthesis and release of these mediators. In animals, a single intravenous injection of IL-1 decreases mean arterial pressure, lowers systemic vascular resistance, and induces leukopenia and thrombocytopenia. In humans, the intravenous administration of IL-1 also rapidly decreases blood pressure and doses of 300 ng or more per kilogram of body weight may cause severe hypotension. The therapeutic advantage of blocking the action of IL-1 resides in preventing its deleterious biological effects without interfering with the production of molecules that have a role in homeostasis. The present inventive compounds address this need, identified by Dinarello et al., by inhibiting cellular signaling only through the IL-1 Type I receptor and not through the IL-1 Type II receptor.

With regard to rheumatoid arthritis, Dinarello and Wolff state: "Interleukin-1 is present in synovial lining and synovial fluid of patients with rheumatoid arthritis, and explants of synovial tissue from such patients produce IL-1 in vitro. Intraarticular injections of interleukin-1 induce leukocyte infiltration, cartilage breakdown, and periarticular bone remodeling in animals. In isolated cartilage and bone cells in vitro, interleukin-1 triggers the expression of genes for collagenases as well as phospholipases and cyclooxygenase, and blocking its action reduces bacterial-cell-wall-induced arthritis in rats." Therefore, the inventive compounds, as IL-1 antagonists, are useful to treat and prevent rheumatoid arthritis.

With regard to inflammatory bowel disease, ulcerative colitis and Crohn's disease are characterized by infiltrative lesions of the bowel that contain activated neutrophils and macrophages. IL-1 can stimulate production of inflammatory eicosanoids such as prostaglandin $E_2$ ($PGE_2$), leukotriene $B_4$ ($LTB_4$) and IL-8, an inflammatory cytokine with neutrophil-chemoattractant and neutrophil-stimulating properties. Tissue concentrations of PGE2 and LTB4 correlate to severity of disease in patients with ulcerative colitis, patients with inflammatory bowel disease having high tissue concentrations of IL-1 and IL-8. Therefore, an IL-1 antagonist, such as the inventive compounds, would be effective to treat inflammatory bowel disease.

With regard to acute and chronic myelogenous leukemia, there is increasing evidence that IL-1 acts as a growth factor for such tumor cells. Therefore, the inventive compounds should be effective to prevent the growth of worsening of disease for acute and chronic myelogenous leukemias.

Insulin-dependent diabetes mellitus (IDDM) is considered to be an autoimmune disease with destruction of beta cells in the islets of Langerhans, mediated by immunocompetent cells. Islets of animals with spontaneously occurring IDDM (e.g., BB rats or NOD mice) have inflammatory cells that contain IL-1. Therefore, the inventive compounds should be useful for the preventing and treating IDDM.

IL-1 also plays a role in atherosclerosis development. Endothelial cells are a target of IL-1. IL-1 stimulates proliferation of vascular smooth muscle cells. Foam cells, isolated from fatty arterial plaques from hypercholesterolemic rabbits, contain IL-1β and IL-1β messenger RNA. The uptake of peripheral blood monocytes results in initiation of IL-1 production by these cells. IL-1 also stimulates production of PDGF. Taken together, IL-1 plays a part in the development of atherosclerotic lesions. Therefore, an IL-1 antagonist, such as the inventive compounds should be useful in preventing and treating atherosclerosis.

IL-1 activates (through the Type I IL-1 receptor) a lyso-PA acyltransferase (LPAAT) and phosphatidate phosphohydrolase within 5 seconds of cell (for example, human mesangial cells, HMC) exposure to this cytokine. As discussed in detail above, activation of both enzymes results in production of PA species with sn-1 and sn-2 unsaturated acyl groups, with the majority of sn-2 acyl chains being polyunsaturated. Both IL-1 and a product of LPAAT, 1,2-sn-dilinoleoyl PA, activate a signaling pathway involving hydrolysis of PE to PA. This reaction is followed by dephosphorylation of PA to produce both 1,2-sn-diacylglycerol, and 1-o-alkyl, or 1-o-alkenyl,acylglycerol (AAG) species. The inventive compounds exert their activity by inhibiting one or both enzymes at an inner leaflet of the plasma membrane. Therefore, appropriate in vitro models for drug activity may measure inhibition of stimulation caused by a proinflammatory cytokine or other inflammatory cellular signal.

The generation of the sn-2 unsaturated PA fraction by LPAAT serves to activate either G-proteins, or acts directly upon PLD through alteration of its lipid microenvironment. Activation of LPAAT and generation of the sn-2-unsaturated PA species is an energy sensitive pathway of PLD. This provides a mechanism for a limited-receptor system to amplify a signal and generate a cellular response by rapid synthesis of small amounts of PA. Uptake of di-unsaturated PA, which is less than about 0.1% of total membrane lipid mass, is sufficient to activate PLD activity. This quantity of PA is similar to that endogeneously synthesized by LPAAT. The PA-stimulated PLD acts upon PE, which should be localized to the inner leaflet of the cell membrane, enriched in PE relative to the outer leaflet. Therefore, the cellular inflammatory response to IL-1 is mediated by the pathway: IL-1R→PA→(PLD)→PE. Whereas a localized tissue response is: lysoPA→PI→PKC→(PLD)→PC. The PLD species are likely to be different isozymes. The second messenger pathway whose activation is inhibited by the inventive compounds is not a PI-derived pathway and does not involve PKC in the time courses of inhibition. PKC is acutely activated by PI-derived DAG, but chronic activation (i.e., >30 minutes) is maintained by PC-derived PA generated by PC-directed PLD. Therefore, the pathway inhibited by the inventive compounds is PE-directed and not PC-directed. Moreover, the PE-directed PLD favors substrates with sn-2 long-chain unsaturation.

DAG and PA are upregulated in oncogenically transformed cells. For example, activating ras mutations result in increased generation of DAG upon stimulation with mitogens, although the sources of DAG differ between experimental systems. In nontransformed renal mesangial cells, IL-1β stimulation increased PLA2 and LPAAT activation, resulting in generation of sn-2 unsaturated PA and subsequent hydrolysis to DAG by phosphatidate phosphohydrolase. The ras transformation in NIH/3T3 cells upregulates serum-stimulated generation of DAG and PA. Particular species of DAG that is stimulated by serum is dioleoyl and of PA are dilinoleoyl and dioleoyl. This upregulation occurs over 4–12 hours and pretreatment of cells with an inventive compound, or PTX, blocks generation of these phospholipid second messengers. The inhibition occurs either through suppressing the generation of PA de novo from lysoPA, or through inhibition of one or both arms of the Lands cycle. The coordinate increase of lysoPA in the setting of diminished PA/DAG production suggests inhibition of transacylation of a precursor lipid. Therefore, the ras transformation mediates an upregulation of PA through indirect stimulation of PLA2 and/or LPAAT activity. The inventive compounds inhibit the conversion of the upregulated lysoPA to PA and subsequently block the phenotypic changes induced by PAIDAG in the membrane.

The ability of the inventive compounds to inhibit generation of unsaturated phospholipids is mirrored by the ability of inventive compounds to inhibit proliferation and tumorogenicity of ras-transformed cells in vitro and in vivo. PTX inhibits ras-transformed NIH/3T3 cells more than parental cells. This inhibition is reversible and is not associated with significant cytotoxicity.

Excessive or unregulated TNF (tumor necrosis factor) production is implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever, myalgias due to infection such as influenza, cachexia secondary to infection, AIDS or malignancy, AIDS, other viral infections (e.g., CMV, influenza, adenovirus, herpes family), keloid formation, scar tissue formation, Crohn's disease, ulcerative colitis, or pyresis. The inventive compounds or pharmaceutically acceptable salts thereof can be used in the manufacture of a medicament for the prophylactic or therapeutic treatment of any disease state in a human or other mammal, which is exacerbated or signaled through the present second messenger cellular phospholipid-based signaling pathway and by excessive or unregulated production of "first messenger" inflammatory cytokines such as TNF or IL-1. With regard to TNF first messenger signaling, there are several disease states in which excessive or unregulated TNF production by monocytes/macrophages is implicated in exacerbating or causing the disease. These include, for example, neurodegenerative diseases such as Alzheimers disease, endotoxemia or toxic shock syndrome (Tracey et al., *Nature* 330:662, 1987 and Hinshaw et al., *Circ. Shock* 30:279, 1990); cachexia (Dezube et al., *Lancet* 355:662, 1990), and adult respiratory distress syndrome (Miller et al., *Lancet* 2(8665):712, 1989). The inventive compounds may be used topically in the treatment of prophylaxis of topical disease states mediated or exacerbated by excessive TNF or IL-1, such as viral infections (herpes or viral conjunctivitis), psoriasis, fungal or yeast infections (ringworm, athletes foot, vaginitis, dandruff, etc.) or other dermatologic hyperproliferative disorders. High TNF levels have been implicated in acute malaria attacks (Grau et al., *N. Engl. J. Med.* 320:1585, 1989), chronic pulmonary inflammatory diseases such as silicosis and asbestosis (Piguet et al., *Nature* 344:245, 1990, and Bissonnette et al., *Inflammation* 13:329, 1989), and reperfusion injury (Vedder et al., *Proc. Natl. Acad. Sci. USA* 87:2643, 1990).

The compounds of the invention can inhibit certain VEGF (vascular endothelial growth factor), FGF (fibroblast growth factor) and PDGF (platelet derived growth factor) effects in vivo, such as inhibition of angiogenesis or restenosis. For example, Ferns et al., *Science* 253:1129, 1991, have shown that neointimal smooth muscle chemotaxis and angioplasty are inhibited in rats using a neutralizing antibody to PDGF. Also, Jawien et al., *J. Clin Invest.* 89:507, 1992, have shown that PDGF promotes smooth muscle migration and intimal thickening in a rat model of balloon angioplasty. Inhibition of the PDGF-mediated effects following balloon angioplasty by the inventive compounds is the pharmacological rationale for using the inventive compounds as therapeutic agents to prevent restenosis. The inventive compounds also inhibit atherogenesis because increased levels of PDGF expressed by macrophages are associated with all phases of atherogenesis (Ross et al., *Science* 248:1009, 1990). Further, many human tumors express elevated levels of either PDGF, FGF, receptors for FGF or PDGF, or mutated cellular oncogenes highly homologous to these growth factors or their receptors. For example, such tumor cell lines include sarcoma cell lines (Leveen et al., *Int. J. Cancer* 46:1066, 1990), metastatic melanoma cells (Yamanishi et al., *Cancer Res.* 52:5024, 1992), and glial tumors (Fleming et al., *Cancer Res.* 52:4550, 1992).

The inventive compounds are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

In Vitro Assays for Physiologic and Pharmacologic Effects of the Inventive Compounds Various in vitro assays can be used to measure effects of the inventive compounds to module immune activity and have antitumor activity using a variety of cellular types. For example, a mixed lymphocyte reaction (MLR) provides a valuable screening tool to determine biological activity of each inventive compound. In the MLR, PBMCs (peripheral blood mononuclear cells) are obtained by drawing whole blood from healthy volunteers in a heparinized container and diluted with an equal volume of hanks balanced salt solution (HBSS). This mixture is layered on a sucrose density gradient, such as a Ficoll-Hypaque® gradient (specific gravity 1.08), and centrifuged at 1000 ×g for 25 minutes at room temperature or cooler. PBMC are obtained from a band at a plasma-Ficoll interface, separated and washed at least twice in a saline solution, such as HBSS. Contaminating red cells are lysed, such as by ACK lysis for 10 min at 37 ° C., and the PBMCs are washed twice in HBSS. The pellet of purified PBMCs is resuspended in complete medium, such as RPMI 1640 plus 20% human inactivated serum. Proliferative response of PBMC to allogeneic stimulation is determined in a two-way MLR performed in a 96-well microtiter plate. Briefly, approximately $10^5$ test purified PBMC cells in 200 μl complete medium are co-cultured with approximately $10^5$ autologous (control culture) or allogeneic (stimulated culture) PBMC cells, wherein the allogeneic cells are from HLA disparate individuals. Varying doses of compounds (drug) are added at the time of addition of cells to the microtiter plate. The cultures are incubated for 6 days at 37° C. in a 5% $CO_2$ atmosphere. At the conclusion of the incubation tritiated thymidine is added (for example, 1 μCi/well of 40 to 60 Ci/mmole) and proliferation determined by liquid scintillation counting.

A thymocyte costimulator assay is conducted to evaluate the inventive compounds to inhibit activation and proliferation of thymocytes caused by stimulation with Con A and interleukin-1 (IL-1), or interleukin-1 (IL-2). Thymuses are obtained from mice (e.g., female Balb/C mice) and the thymuses are removed and dissociated into culture media (e.g., RPMI 1640 without serum supplementation). The dissociated thymus tissue and cell suspension is transferred to centrifuge tubes and allowed to settle, washed with HBSS and resuspended in serum-supplemented culture media (e.g., RPMI 1640 with 10% fetal calf serum). Any contaminating red cells are lysed, and viable cells are resuspended and counted. Thymocytes are plated (e.g., 96-well plates at a density of $2 \times 10^5$ cells/well) and a stimulating agent, such as Con A, IL-1 (e.g., IL-1α) or IL-2 is added to the well. The cells are incubated for 4 days at 37° C. On the fourth day, the cells are pulsed with tritiated thymidine and cell proliferation determined. Inventive compounds are added at the time of stimulating agent addition.

Each inventive compound is investigated for cytotoxicity to determine appropriate doses for biological activity assays and to prevent cytotoxic reactions in in vitro assays when characterizing activity. Cells (e.g., NIH-3T3, Ras transformed 3T3 cells, malignant melanoma LD2 cells, etc.) are added to microtiter plates and drug is added about two days after plating. Cell viability is determined using a fluorescent viability stain (e.g., 2', 7'-bis-(2-carboroxyethyl)-5-(and -6)-carboxyfluorescein acetoxymethyl ester, BCECF excitation 488 nm and emission 525 nm) 24, 48 or 72 hours after addition of the drug.

Another assay for measuring activity of the inventive compounds involves determining PDGF (platelet derived growth factor) proliferative response using human-derived stromal cells. Human stromal cells are plated (e.g., about 2000 cells per well) in defined media (e.g., 69% McCoy's, 12.5% fetal calf serum, 12.5% horse serum, 1% antibiotics, 1% glutamine, 1% vitamin supplement, 0.8% essential amino acids, 1% sodium pyruvate, 1% sodium bicarbonate, 0.4% non-essential amino acids and 0.36% hydrocortisone). Two to three days later, the stromal cells are starved in serum-free media. Twenty four hours later, the cells are treated with a stimulating agent, such as PDGF-AA, PDGF-BB or basic FGF (fibroblast growth factor) with or without IL-1α or TNF, and tritiated thymidine. Cell proliferation is determined by liquid scintillation counting.

A B-cell proliferation assay determines the effect of the inventive compounds on inhibiting proliferation of stimulated B-cells, stimulated by an anti-mu antibody (40 µg/mi), IL-4 or PMA (2.5 nM). Ramos B-cell tumor cells or murine splenocytes can be incubated with a stimulating agent, an inventive compound and tritiated thymidine to measure inhibition of cell proliferation caused by the stimulating agent.

Drug inhibitory activity can also be measured by determining levels of vascular cell adhesion molecule (VCAM) in stimulated cells. Early passage human umbilical vein endothelial cells (HUVEC) (obtained from commercial suppliers such as Cell Systems, Inc. or Clonetics) are cultured in media (e.g., Hepes buffered media, Cell Systems) containing 10% fetal bovine serum, and supplemented with a stimulating agent, such as fibroblast growth factor (acidic FGF, Cell Systems, Inc.) or TNF. The cells are plated into wells of a microtiter plate (e.g., $5 \times 10^4$ per well) and allowed to incubate at 37° C. for 72 hrs. The resting cells are removed (e.g., 20–30 min treatment with 0.4% EDTA), washed in media (e.g., phosphate buffered saline plus 0.1% bovine serum albumin with 0.01% sodium azide) and labeled on ice with a monoclonal antibody ("first antibody") recognizing human VCAM (e.g., 1 µg of a murine monoclonal antibody recognizing human VCAM Genzyme). After 60 min on ice, the cells are washed (preferably twice) with cold wash media and incubated with an antibody that recognizes the first antibody, (e.g., 1 µg of goat anti-mouse IgG conjugated with phycoerythrin, CalTag, Inc.). After 30 min on ice, the cells are washed twice and analyzed on a flow cytometer (Coulter Elite®) at appropriate emission and excitation wavelengths (e.g., for phycoerythrin use excitation at 488 nm and emission at 525 nm).

One in vitro assay measures inhibition of the relevant enzymes lysophosphatidic acid acyltransferase (LPAAT) and phosphatidic acid phosphoryl hydrolase (PAPH). The assay involves incubating of target cells with a primary stimulus (e.g., a variety of cytokines, growth factors, oncogene products, putative therapeutic agents, irradiation, viral infection, toxins, bacterial infection and the products thereof, and any stimulus which, if not counteracted, has a deleterious effect on the target cell) in the presence or absence of an inventive compound at varying dosage levels. Target cells include, for example, subcellular entities, such as, microsomes derived from mesenchymal and/or ectodermal cells, particularly microsomes from marrow stromal cells or human or rat mesangial cells; microsomes or synaptosomes derived from bovine brain; plasma membrane-enriched microsomes, plasma membranes derived as described in Bursten et al. (*J. Biol. Chem.* 226:20732–20743, 1991), or detergent-solubilized microsomes; synaptosomes, and membranes or other cell preparations solubilized using, for example, NP-40, Miranal, SDS or other neutral detergents; and detergent-solubilized or further purified preparations of cell proteins, including the proteins LPAAT and/or PAPH. After incubation for short periods of time, cell lipids are extracted and assayed by thin layer chromatography according to standard procedures. Briefly, lipids are extracted using, for example, chloroform:methanol 2:1 (v/v), and the extracts are then subjected to HPLC as described in Bursten and Harris, *Biochemistry* 30:6195–6203, 1991. A Rainin® mu-Porasil column is used with a 3:4 hexane:propanol organic carrier and a 1–10% water gradient during the first 10 minutes of separation. Detection of the peaks in the elution pattern is by absorption in the range of ultraviolet which detects isolated double bonds. The relevant peaks of unsaturated PA and DAG are shown in the elution pattern. It is important to note that the assay method permits discrimination between various forms of PA and DAG so that those relevant to the pathway affected by the (R) or (S) compounds of the invention can be measured directly. Confirmation of the nature of the acyl substituents of these components is accomplished using fast-atom bombardment mass spectroscopy. Thus, the relevant unsaturated (non-arachidonic) PA and DAG subspecies may be detected. The time periods employed are 5–60 seconds after stimulation with the primary stimulus, such as a cytokine. This technique permits assessment of the levels of various lipid components as a function of time.

An inventive compound can be assayed for activity protecting TNF-mediated cytotoxicity. In this assay, L929 murine fibroblast cells ($10^4$ cells per well) are incubated with either compounds at varying doses and media control for two hrs. TNF-α (R&D Systems) is added at a concentration of 500 pg/ml, which is four times the LD50 of TNF (125 pg/ml). The cells plus (or minus) drug plus TNF were incubated for 40 hrs at 37° C. The media is removed and replaced with fresh media containing 2% serum and 10 µg/ml of BCECF fluorescent dye and incubated for 30 min. The fluorescent dye-containing media is removed and replaced with PBS (phosphate buffered saline) and each well was assayed for fluorescence.

Another assay measures the effects of drug to inhibit adhesion of U937 cells to TNF-activated HUVEC cells In this experiment, HUVEC cells are induced with human TNF-α (20 ng/ml) and drug at varying concentrations for 14–16 hrs. U937 cells (a human monocyte cell line) are incubated and labeled with BCECF (10 µg/ml), a fluorescent dye. The U937 cell preparation ($2.5 \times 10^4$ cells per well) is layered on top of the activated HUVEC cells. The cells are reverse spun to remove partially adhering and nonadhering U937 cell. The adherent U937 cells are measured by fluorescence on a fluorescent plate reader.

Compounds of the Invention

The invention is directed to the use of acetal-and ketal-substituted therapeutic compounds. The inventive acetal-and ketal-substituted compounds are useful in a large variety of therapeutic indications for treating or preventing disease. In particular, the inventive compounds and pharmaceutical compositions thereof provide therapy for diseases mediated by intracellular signaling through specific intracellular signaling pathways, more specifically, the pathways herein discussed.

The inventive compounds have at least one acetal-or ketal-containing side chain and are preferably cyclic or heterocyclic compounds. The inventive compounds and pharmaceutical compositions thereof have the formula:

CORE MOIETY—(R)$_j$ including resolved enantiomers and/or diastereomers, hydrates, salts, solvates and mixtures thereof, wherein j is an integer from one to three, the core moiety is non-cyclic or cyclic and R may be selected from among: hydrogen, halogen (preferably bromine, chlorine, fluorine and iodine), hydroxyl, amino, substituted or unsubstituted $C_{(1-6)}$, alkyl, $C_{(2-6)}$ alkenyl, cyclic or heterocyclic groups, and groups having a structure prescribed by formula I, below.

Preferred R substituents having a structure other than prescribed by formula I below include, but are not limited to, methyl, ethyl, isopropyl, n-propyl, isobutyl, n-butyl, t-butyl, 2-hydroxyethyl, 3-hydroxypropyl, 3-hydroxy-n-butyl, 2-methoxyethyl, 4-methoxy-n-butyl, 5-hydroxyhexyl, 2-bromopropyl, 3-dimethylaminobutyl, 4-chloropentyl, and the like. Particularly preferred R are ethyl, methyl, or hydrogen.

In the inventive compounds, at least one R has the formula I:

—(CH$_2$)$_n$—C—(R$_1$)$_3$,  I wherein n is an integer from three to twenty; R$_1$ is selected from among: hydrogen; halogen; hydroxide; substituted or unsubstituted $C_{(1-6)}$ alkyl, $C_{(1-6)}$ alkoxy, $C_{(2-6)}$ alkenyl, cyclic or heterocyclic group; —OR$_2$, R$_2$ being hydrogen or a substituted or unsubstituted $C_{(1-6)}$ alkyl, $C_{(2-6)}$ alkenyl, cyclic or heterocyclic group; —(CH$_2$)$_p$—C(R$_3$)$_3$ (wherein p is zero or an integer from one to ten, R$_3$ is hydrogen, halogen, hydroxide, substituted or unsubstituted $C_{(1-6)}$ alkyl, $C_{(1-6)}$ alkoxy, $C_{(2-6)}$ alkenyl, cyclic or heterocyclic group, or —OR$_2$, R$_2$ being defined above); and at least two R$_1$ or two R$_3$ are —OR$_2$ or jointly form —(CH$_2$)S—O—C(R$_4$)$_2$—O—(CH$_2$)t— (wherein s and t are independently zero, one or two, a sum of s and t is less than three, and R$_4$ is hydrogen, halogen or substituted or unsubstituted C($_{1-6}$) alkyl, $C_{(2-6)}$ alkenyl, cyclic or heterocyclic group). In the inventive compounds, no more than one R$_2$, corresponding to the at least two R$_1$ or two R$_3$ which are —OR$_2$, is hydrogen and a third R$_1$ or third R$_3$, bonded to the same —C as both the at least two R$_1$ or two R$_3$, is other than —OR$_2$.

Optionally, two terminal R$_2$ of —C(OR$_2$)$_2$ may join to form a heterocyclic group having from four to seven ring atoms, the O of each —OR$_2$ being a hetero atom of the heterocycle. Also, (CH$_2$)$_n$ and/or (CH$_2$)$_p$ optionally may have one or two unsaturated bonds (preferably in a cis configuration) or be interrupted by at least one oxygen atom.

Preferably, n is an integer from about three to about eighteen, more preferably, an integer from about three to about seven. In especially preferred compounds, R$_1$ of —C(R$_1$)$_2$ are both —OR$_2$ and the two R$_2$ join to form a heterocyclic group having five ring atoms, the —C and each O of —C(OR$_2$)$_2$ comprising three of the five ring atoms. Alternatively, R$_1$ of —C(R$_1$)$_2$ jointly form —(CH$_2$)$_s$—O—C(R$_4$)$_2$—O—(CH$_2$)$_t$, wherin s is one, t is zero and one or both of R$_4$ are hydrogen or unsubstituted $C_{(1-6)}$ alkyl, most preferably, both R$_4$ being hydrogen or methyl.

Although other possible substituents are within the scope of the inventive compounds, representative substituents for any of R/R$_1$/R$_2$/R$_3$/R$_4$ substituted $C_{(1-6)}$ alkyl, $C_{(1-6)}$ alkoxy, $C_{(2-6)}$ alkenyl, cyclic or heterocyclic groups may be selected from among: amide, primary, secondary and tertiary amine, $C_{(2-8)}$ alkenyl, $C_{(1-8)}$ alkyl (including, e.g., branched and unbranched alkyl or alkenyl groups), $C_{(1-8)}$ alkoxy, azide, carbonate, carbonyl, carboxylic acid, cyanide, $C_{(1-8)}$ haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate, thioester, thiolester, thiol, thiourea and urea.

Representative R/R$_1$/R$_2$/R$_3$/R$_4$ cyclic groups may be, but are not limited to: anthracene, bicyclo|4.4.0|decane, bicyclo |2.2.1|heptane, bicyclo|3.2.0|heptane, bicyclo|4.1.0| heptane, bicyclo|2.2.1|hexane, bicyclo|4.3.0|nonane, bicyclo |2.2.2|octane, biphenyl, cyclopentadiene, cyclopentane, cyclobutane, cyclobutene, cycloheptane, cyclohexane, cyclooctane and cyclopropane, 1,2-diphenylethane, fluorene, indene, phenyl, terphenyl, napthalene, phenanthrene, terphenyl, toluene and xylene. Due primarily to availability and ease of synthesis, more preferred R/R$_1$/R$_2$/R$_3$/R$_4$ cyclic groups include less complex ring systems, such as, for example, cyclopentane and cyclohexane, cyclopentadiene, phenyl, indene, toluene and xylene.

R/R$_1$/R$_2$/R$_3$/ R$_4$ heterocyclic groups may include azetidine, benzofuran, benzothiophene, carbazole, furan, glutarimide, indole, isoquinolone, lactam, lactone, oxazole, oxetane, oxirane, pyrrolidine, pyran, piperidine, pyridine, pyrrole, quinolone, tetrahydrofuran, tetrahydropyran, tetrahydrothiophene, thiophene, derivatives thereof and the like. Preferred R/R$_1$/R$_2$/R$_3$/R$_4$ heterocyclic groups are furan, indole, thymine and xanthine, although other heterocyclic groups are within the scope of the inventive compounds.

A non-cyclic core moiety may include, but is not limited to, for example, acetamide, amide, amine, amino acid (one or two), carboxide, ester, terminal halogen or hydrogen atom, hydroxide, glutaric acid, glycine derivative, ketone, phosphate, phosphonate, sulfate, sulfonate, sulfone, sulfoxide, simple ionic functional group, thiol or thiolester. Exemplary core moiety amino acids may include one or more of the following: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The non-cyclic core moiety may preferably be an amide, carboxyl ester, carboxide, hydrogen, hydroxide or a dipeptide comprising two amino acids selected from the foregoing exemplary list. A non-cyclic, halogen, core moiety may be, for example, bromine, chlorine, fluorine and iodine.

A cyclic core may be at least one five-to seven-member non-heterocyclic ring or a heterocycle. The at least one five-to seven-membered non-heterocyclic ring may preferably have from one to three, five-to six-membered ring structures in a predominantly planar configuration. For example, the core moiety may be selected from the group consisting of substituted or unsubstituted benzene; biphenyl; cyclohexane; cyclohexanedione; cyclopentanedione; napthlalene; phenol; salicylic acid and derivatives thereof; stilbene or tricyclododecane.

Although other heterocyclic cores are within the scope of the invention, the following cores are representative heterocyclic cores: substituted or unsubstituted barbituric acid; benzamide; lactam; glutarimide; homophthalimide; hydrophthalimide; imidazole; imidazole amide; indomethacin; isocarbostyril; lumazine; N-alkylheterocyclic; N-heterocyclic; pteridine; pthalimide; piperidine; pyridine; pyrimidine; pyrrole amide; quaternized N-heterocyclic; quinolizinedione; quinazolinone; quinolone; recorsinol; succinimide; theobromine; thymine; triazine; uric acid; uracil; vitamins A, E or K; or xanthine.

Non-limiting, representative substituents for the non-heterocyclic ring and heterocyclic cores may include, but are not limited to: amide, primary, secondary and tertiary amine, $C_{(2-8)}$ alkenyl, $C_{(1-8)}$ alkyl (including, e.g., branched and unbranched alkyl or alkenyl groups), $C_{(1-8)}$ alkoxy, azide, carbonate, carbonyl, carboxylic acid, cyanide, $C_{(1-8)}$, haloalkyl (including, e.g., mono-, di- and tri-haloalkyl substituents, such as trihalomethyl), isocyanate, isothiocyanate, phosphate, phosphonate, primary, secondary or tertiary alcohol (including, e.g., any one of various diols, methanol, butanol, 1-cyclopentanol, ethanol, 2-ethyl-3-methyl-1-propanol, pentanol, propanol, and methylcyclohexanol), sulfonate, sulfone, sulfoxide, thioamide, thiocarbonate, thioester, thiolester, thiol, thiourea and urea.

Preferred cyclic and heterocyclic cores include substituted or unsubstituted glutarimide, methylthymine, methyluracil, thymine, theobromine, uracil and xanthine, most preferably halogen-substituted xanthine. Exemplary preferred cores include: 1,3-cyclohexanedione, 1,3-cyclopentanedione; 1,3-dihydroxynaphthalene; 1-methyllumazine; methylbarbituric acid; 3,3-dimethylglutarimide; orotic acid; tetra or hexahydrophthalimide; orthophenol; prostacyclin; 2-hydroxypyridine; methyldihydroxypyrazolopyrimidine, specifically, 1,3-dimethyldihydroxypyrazolo|4,3-d|pyrimidine; methylpyrrolopyrimidine; 1-methylpyrrolo |2,3-d| pyrimidine; 1,3-dihydroxynapthalene; 1-pyrrole amides; 2-pyrrole amides; 3-pyrrole amides; 1,2,3,4-tetrahydroisoquinolone; 1-methyl-2,4(1H,3H)-quinolizinedione (1-methylbenzoyleneurea); quinazolin-4(3H)-one; sulindac; dihydrothymine; alkyl-substituted (C1–6) thymine; 2,4-dioxohexahydro-1,3,5tetrazine; methylthymine; alkyl-substituted (C1–6) uracil; uracil fused to naphthalene; 6-aminouracil; 1-methyl-5,6-dihydrouracil; 1-methyluracil; 5- and/or 6-position substituted uracils (such as, for example, 5-bromouracil); B-ionone as vitamin A; 2,6,6-methyl-1-cyclohexene-1-acetaldehyde as vitamin A; tetralone to vitamin K; 1,7-dimethylxanthine, 3,7-dimethylxanthine; 3-methylxanthine; 3-methyl-7-methylpivaloylxanthine; 8-substituted xanthines (having substituents such as N or S); and 7-methylhypoxanthine.

Preferably, R is bonded to a nitrogen of the core moiety, most preferably the core moiety is xanthine and R of formula I is bonded to an $N_1$ xanthine nitrogen and $N_3$ and $N_7$ xanthine nitrogens are independently substituted by a member selected from the group consisting of hydrogen, methyl, fluoro, chloro and amino. Representative, preferred inventive compounds are compounds of formula II:

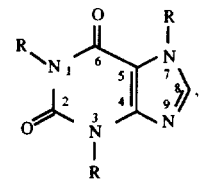

wherein R is defined above. A single R of formula I above may be bonded to the $N_1$ xanthine nitrogen or each of two R of formula I may be bonded to $N_1$ and $N_7$ xanthine nitrogens, respectively, in a covalent bond, or by an ether, ester, or peptide linkage. Preferably, two $R_1$ of —$C(R_1)_2$ are both —$OR_2$ and the two $R_2$ join to form a heterocyclic group having five ring atoms, the —C and each O of —$C(OR_2)_2$ comprising three of the five ring atoms. Alternatively, the two $R_1$ of —$C(R_1)_2$ jointly form —$(CH_2)_S$—O—$C(R_4)_2$—O—$(CH_2)_t$, wherein s is one and t is zero and one or both of $R_4$ are hydrogen or unsubstituted $C_{(1-6)}$ alkyl, most preferably both $R_4$ being hydrogen or methyl. Especially preferred are compounds wherein $(CH_2)_n$, has one cis double bond between the third and fourth carbon atoms, counting from a ring nitrogen toward the end of the R of formula I. Remaining preferred R substituents of formula II may be selected from the group consisting of hydrogen, methyl, fluoro, chloro and amino.

The present invention further provides pharmaceutical compositions suitable for normal routes of therapeutic administration, providing effective compound dosages. The inventive pharmaceutical compositions comprise inventive compound and a pharmaceutically acceptable excipient, formulated for, e.g., parenteral, oral, topical and other known methods of pharmaceutical administration.

More specifically, the invention provides for a pharmaceutical composition comprising one or a plurality of inventive compounds and a pharmaceutically acceptable carrier or excipient. The individuals to be treated with an inventive compound or inventive pharmaceutical composition may either be contacted with the compound of the invention in vitro culture, in an extracorporeal treatment, or by administering (oral, parenteral or topical) the compound of the invention or pharmaceutical composition to a subject whose cells are to be treated.

Illustrative compounds of the invention include both cis and trans enantiomers and/or diastereomers, hydrates, salts, solvates and mixtures thereof, are representative only and are not intended as limiting the disclosure herein in any way:

1567  1-(6-Oxohexyl)-3,7-dimethylxanthine ethylene acetal

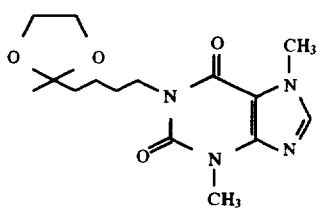

1573 1-(9,10-Methylenedioxydecyl)-3,7-dimethylxanthine

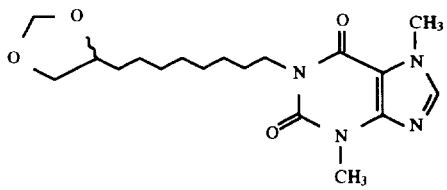

1590 1-(5,6-Methylenedioxyhexyl)-3,7-dimethylxanthine

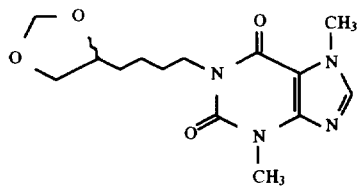

1591 1-(5,6-Propylenedioxyhexyl)-3,7-dimethylxanthine

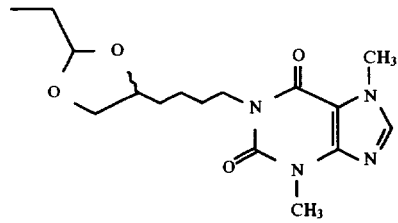

Uses of the Inventive Compounds

The compounds of the invention provide a mechanism to maintain homeostasis in cells contacted by primary stimuli through mitigating the effects of these primary stimuli on the secondary signaling pathways invoked within seconds of the primary stimulus. For example, administration of the inventive compounds in vivo or ex vivo provide a method to modify cellular behavior which method comprises contacting cells whose behavior is to be modified with an effective amount of an inventive compound or a pharmaceutical composition thereof wherein said method is: (1) a method to inhibit proliferation of tumor cells and said amount is sufficient to inhibit said proliferation; or (2) a method to promote differentiation of hematopoietic stem cells into red blood cells, platelets, lymphocytes, and granulocytes, and said amount is sufficient to promote said proliferation; or (3) a method to suppress activation of T-cells by antigen or IL-2 stimulation, and said amount is sufficient to promote said activation; or (4) a method to suppress activation of monocyte/macrophage cells by endotoxin, TNF, IL-1 or GM-CSF stimulation and said amount is sufficient to suppress said activation; or (5) a method to enhance the resistance of mesenchymal cells to the cytotoxic effect of tumor necrosis factor and said amount is sufficient to enhance said resistance; or (6) a method to suppress antibody production of B-cells in response to an antigen, IL-4 or CD40 ligand and said amount is sufficient to suppress said antibody production; or (7) a method to inhibit the proliferation of smooth muscle cells in response to growth factors capable of stimulating said proliferation and said amount is sufficient to inhibit said proliferation; or (8) a method to lower systemic vascular resistance conferred by endothelial cells and said amount is sufficient to reduce the release of hypertension-inducing substances; or (9) a method to lower systemic vascular resistance induced by endothelial cells and said amount is sufficient to enhance the release of anti-hypertensive substances; or (10) a method to lower expression of adhesion molecules induced by enhancers thereof, and said amount is sufficient to lower said expression; or (11) a method to suppress the activation of T-cells by HIV and said amount is sufficient to suppress said activation thus inhibiting viral replication; or (12) a method to inhibit the proliferation of kidney mesangial cells in response to stimulation by IL-1 and/or mip-1α and/or PDGF and/or FGF and said amount is sufficient to inhibit said proliferation; or (13) a method to enhance the resistance of kidney glomerular or tubular cells to cyclosporin A or amphotericin B and said amount is sufficient to enhance said resistance; or (14) a method to prevent the suppression of growth stimulatory factor production in TNF-treated bone marrow stromal cells and said amount is sufficient to prevent said suppression; or (15) a method to prevent the release of mip-1α by IL-1, TNF, or endotoxin stimulated monocytes and macrophages; or (16) a method to prevent the release of platelet activating factor by IL-1, TNF, or endotoxin treated megakaryocytes, fibroblastic cells, and macrophages; or (17) a method to prevent the down-regulation of receptors for cytokines in TNF-treated hematopoietic progenitor cells and said amount is sufficient to prevent said down-regulation; or (18) a method to suppress the production of metalloproteases in IL-1-stimulated or TNF-stimulated glomerular epithelial cells or synovial cells and said amount is sufficient to enhance said production; or (19) a method to enhance the resistance of gastrointestinal or pulmonary epithelial cells to cytotoxic drugs or radiation and said amount is sufficient to enhance said resistance; or (20) a method to enhance the antitumor effect of a non-alkylating antitumor agent and said amount is sufficient to enhance said effect, or (21) a method to inhibit the production of osteoclast activating factor in response to IL-1, and said amount is sufficient to inhibit said production, or (22) a method to inhibit degranulation in response to IgE, and said amount is sufficient to inhibit said degranulation, or (23) a method to enhance the release of adrenergic neural transmitters, dopamine, norepinephrine, or epinephrine, or the neurotransmitter, acetylcholine, and said amount is sufficient to enhance said release, or (24) a method to modulate the post-synaptic "slow current" effects of the adrenergic neurotransmitters dopamine, epinephrine, or norepinephrine, or the neurotransmitter acetylcholine, and said amount is sufficient to modulate such slow currents.

For example, the compounds of the invention are used in connection with patients undergoing bone marrow transplantation (BMT), regardless of whether the BMT is matched allogeneic, mismatched allogeneic, or autologous. Patients receiving autologous transplants are aided by treatment with compounds of the invention even though they do not necessarily need to be administered immunosuppressive agents, since they do not develop graft-versus-host disease (GVHD). However, the toxic effect of the chemotherapy or radiation therapy used in connection with the disease, in response to which the transplantation has been performed, constitutes a negative stimulus with regard to the patients' cells.

In general, all patients undergoing BMT require doses of chemotherapy with or without total body irradiation that exceed the lethal dose for normal bone marrow recovery. This provides the rationale for using either stored patient marrow or donor marrow to rescue the patient. In general, chemotherapy and radiation are delivered to the patient for 7–10 consecutive days before the new or stored bone marrow is infused. The day on which the marrow is given to the patient is referred to as day 0 of the transplant. Previous days on which the patient received chemo/radiation are designated by negative numbers. Subsequent days are referred to by positive numerals.

The median time in which negative responses in BMT recipients occurs is within the first 100 days after transplant. Therefore, statistically, if patients survive through day 100, their chances for continued survival are significantly enhanced. Compounds of Formula I are able to increase the percentage of patients who survive. The percentage of fatalities within the first 100 days that is considered acceptable is 15–20% for "good risk" patients and 30–40% for "high risk". These fatalities are due to the direct effects of high doses of chemo/radiation. In addition, GVHD contributes to the death rate in allogeneic marrow recipients.

Other indications for which it is useful to administer the compounds of the invention include the presence of a tumor burden, a hormone-related disorder, a neurological disorder, an autoimmune disease, inflammation, restenosis, hypertension, unwanted immune response, viral infection, nephritis, mucositis, and various allergic responses. Prevention of allergic responses include prevention of acute allergic response and thus moderation or prevention of rhinorrhea, sinus drainage, diffuse tissue edema, and generalized pruritus. Other symptoms of chronic allergic response include, as well as the foregoing, dizziness, diarrhea, tissue hyperemia, and lacrimal swelling with localized lymphocyte infiltration. Allergic reactions are also associated with leukotriene release and the distal effects thereof, including asthmatic symptoms including development of airway obstruction, a decrease in FEV 1, changes in vital capacity, and extensive mucus production.

Other suitable subjects for the administration of compounds of the invention, include patients being administered cytoreductive agents for the treatment of tumors, such as chemotherapeutic agents or irradiation therapy, as well as treatment with biological response modifiers such as IL-2 and tumor suppressing cells such as lymphokine activated killer cells (LAK) and tumor-infiltrating lymphocytes (TIL cells); patients suffering from neoplasias generally, whether or not otherwise treated including acute and chronic myelogenous leukemia, hairy cell leukemia, lymphomas, megakaryocytic leukemia, and the like; disease states caused by bacterial, fungal, protozoal, or viral infection; patients exhibiting unwanted smooth muscle cell proliferation in the form of, for example, restenosis, such as patients undergoing cardiac surgery; patients who are afflicted with autoimmune diseases, thus requiring deactivation of T and B cells, and patients who have neurological disorders.

The compounds of the invention further are able to decrease enhanced levels of a relevant PA and DAG resulting from stimulation of synaptosomes with acetylcholine and/or epinephrine. This suggests that the effects of the compounds of the invention are to both enhance the release of inhibitory neural transmitters such as dopamine, and to modulate the distal "slow current" effects of such neurotransmitters.

Thus, the drugs of the invention are also useful to raise the seizure threshold, to stabilize synapses against neurotoxins such as strychnine, to potentiate the effect of anti-Parkinson drugs such as L-dopa, to potentiate the effects of soporific compounds, to relieve motion disorders resulting from administration of tranquilizers, and to diminish or prevent neuron overfiring associated with progressive neural death following cerebral vascular events such as stroke. In addition, the compounds of the invention are useful in the treatment of norepinephrine-deficient depression and depressions associated with the release of endogenous glucocorticoids, to prevent the toxicity to the central nervous system of dexamethasone or methylprednisolone, and to treat chronic pain without addiction to the drug. Further, the compounds of the invention are useful in the treatment of children with learning and attention deficits and generally improve memory in subjects with organic deficits, including Alzheimer's patients.

While dosage values will vary, therapeutic efficacy is achieved when the compounds of the invention are administered to a human subject requiring such treatment as an effective oral, parenteral, or intravenous sublethal dose of about 50 mg to about 5000 mg per day, depending upon the weight of the patient. A particularly preferred regimen for use in treating leukemia is 4–50 mg/kg body weight. It is to be understood, however, that for any particular subject, specific dosage regimens should be adjusted to the individual's need and to the professional judgment of the person administering or supervising the administration of the inventive compounds.

Pharmaceutical Formulations

A suitable formulation will depend on the nature of the disorder to be treated, the nature of the medicament chosen, and the judgment of the attending physician. In general, the inventive compounds are formulated either for injection or oral administration, although other modes of administration such as transmucosal or transdermal routes may be employed. Suitable formulations for these compounds can be found, for example, in *Remington's Pharmaceutical Sciences* (latest edition), Mack Publishing Company, Easton, Pa.

The inventive compounds and their pharmaceutically acceptable salts can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect on topical administration will, of course, vary with the compound chosen, the nature and severity of the disease and the discretion of the treatment provider. Parenteral includes intravenous, intramuscular, subcutaneous, intranasal, intrarectal, intravaginal or intraperitoneal administration. Appropriate dosage forms for such administration may be prepared by conventional techniques. A typical parenteral composition consists of a solution or suspension of the inventive compound or a salt thereof in a sterile or non-aqueous carrier optionally containing a parenterally acceptable oil, for example polyethylene glycol, polyvinylpyrrolidone, lecithin, arachis oil, or sesame oil. The daily dosage for treatment of sepsis or another severe inflammatory condition via parenteral administration is suitable from about 0.001 mg/kg to about 40 mg/kg, preferably from about 0.01 mg/kg to about 20 mg/kg of an inventive compound or a pharmaceutically acceptable salt thereof calculated as the free base.

The inventive compounds may be administered orally. The daily dosage regimen for oral administration is suitably from about 0.1 mg/kg to about 1000 mg/kg per day. For administration the dosage is suitably form about 0.001 mg/kg to about 40 mg/kg of the inventive compound or a pharmaceutically acceptable salt thereof calculated as the free base. The active ingredient may be administered from 1 to 6 times a day, sufficient to exhibit activity.

The inventive compounds may be administered by inhalation (e.g., intranasal or oral). Appropriate dosage forms include an aerosol or a metered dose inhaler, as prepared by conventional techniques. The daily dosage is suitably form about 0.001 mg/kg to about 40 mg/kg of the inventive compound or a pharmaceutically acceptable salt thereof calculated as the free base. Typical compounds for inhalation are in the form of a solution, suspension or emulsion that may be administered as a dry powder or in the form of an aerosol using a conventional propellant.

The following examples, which should not be regarded as limiting in any way, illustrate the invention.

EXAMPLE 1

This example illustrates a method for synthesis of inventive compound no. 1567 (chemical name and formula provided above). A reaction mixture of 6-oxohexyltheobromine (140 mg, 0.5 mmol), toluenesulfonyl chloride (20 mg, 0.1 mmol), ethylene glycol (2.2 g, 36 mmol) and toluene (10 ml) was added to a glass reaction vessel. Molecular sieves (1.5 g) were added and the reaction mixture was heated at 100°–110° C. for 6 hours and then stirred at room temperature for 3 days. The reaction mixture was added to saturated sodium bicarbonate (50 ml) and then extracted with dichloromethane (3×40 ml). The organic portions were pooled, dried over sodium sulfate, filtered, and evaporated to leave a crude solid. The crude solid was recrystalized from dichloromethane/petroleum ether to obtain 98 mg (0.3 mmol) pure inventive compound no. 1567 (61% yield).

EXAMPLE 2

This example illustrates a synthesis procedure for inventive compound no. 1573. The synthesis began with a solution of 9-decene-1-ol (3.0 g, 19.2 mmol) in dichloromethane (100 ml) at 0° C. To this solution was added methanesulfonyl chloride (2.2 g, 1.5 ml, 19.2 mmol), followed by triethylamine (2.91 g, 28.8 mmol). After stirring for 15 minutes at 0° C., the reaction mixture was allowed to warm to room temperature. After 2 hours, the reaction mixture was poured into 100 ml of water and extracted with dichloromethane (3×60 ml). The organic portions were combined, dried in sodium sulfate, and evaporated to give 9-decene-1-mesylate as a yellow oil (4.52 g, 100% yield). The mesylate was used without further purification.

Theobromine (3.45 g, 19.2 mmol) was added to a suspension of NaH (461 mg, 19.2 mmol) in DMSO (30 ml). After 15 minutes, 9-decene-1-methanesulfonate (2.25 g, 11 mmol) was added and the reaction mixture was stirred for 18 hours at 25° C., and then for 40 minutes at 100° C. The reaction mixture was poured into 100 ml of water and extracted with dichloromethane (3×50 ml). The organic portions were combined, washed with brine (60 ml), dried with magnesium sulfate, and evaporated to provide a white solid. Recrystalization of this solid (in dichloromethane/ petroleum ether) provided a colorless oil of 1-(9-decenyl)-3,7-dimethylxanthine (3.40 g) at a 56% yield.

A solution of (1-(9-decenyl)-3,7-dimethylxanthine (3.2 g, 10.1 mmol)), 4-methylmorpholine-N-oxide (1.41 g, 12 mmol) and $OsO_4$ (3 drops of a 2.5% solution by weight in tBuOH) in acetone (40 ml) and water (10 ml) was stirred for 24 hours. A saturated solution of sodium dithionite (5 ml) was added to the reaction mixture which was then stirred for 15 minutes. The reaction mixture was extracted with 25 % EtOH/dichloromethane (4×50 ml). The organic layers were combined, dried with sodium sulfate and evaporated to a white solid, which upon recrystalization in ethanol yielded 3.3 g of 1-(9,10-dihydroxydecyl)-3,7-dimethylxanthine (93% yield).

A solution of dimethyl sulfoxide (DMSO, 86 mg, 1.1 mmol) in benzene (10 ml) was cooled to 0° C. and then chlorotrimethyl silane (120 mg, 1.1 mmol) was added. After 10 minutes, 1-(9,10-dihydroxydecyl)-3,7-dimethylxanthine (200 mg, 0.6 mmol, prepared above) was added, and the reaction mixture refluxed for 15 hours. The reaction mixture was poured into water (50 ml) and extracted with dichloromethane (3×40 ml). The organic portions were combined, washed with brine (20 ml), dried over sodium sulfate and evaporated to an off-white solid. The crude solid was recrystalized in dichloromethane/petroleum ether to obtain 104 mg of inventive compound no. 1573 (48% yield) as a white solid.

EXAMPLE 3

This example illustrates a synthesis procedure for inventive compound no. 1590. DMSO (236 mg, 3 mmol) and trimethylsilychloride (0.38 ml, 3 mmol) were added to a glass reaction vessel containing benzene (5 ml) at 0° C. The mixture was stirred for 10 minutes and a white precipitate formed. 5,6-Dihydroxyhexyltheobromine (a metabolite of pentoxifylline) was added as a solid, and the reaction mixture heated to reflux for 16 hours to dissolve the solid. The solvent was removed by rotary evaporation, and water (20 ml) was added to the residue. The residue was extracted with diethyl ether (2×30 ml) and the organic portions were pooled, dried over magnesium sulfate, filtered and evaporated, resulting in crude inventive compound no. 1590. The crude product was purified by column chromatography over silica gel with a mobile phase of methylene chloride, followed by methanol/dichloromethane (4:96) to obtain 320 mg of pure compound no. 1590 (82% yield).

EXAMPLE 4

This example illustrates a synthesis for inventive compound no. 1591 (chemical name and structure above). To a mixture of bromohexene (10.7 g, 66 mmol, available from Aldrich) and sodium hydride (1.58 g, 66 mmol) in dimethylsulfoxide (100 mL) was added theobromine (11.9 g, 66 mmol, available from Sigma). The resulting reaction mixture was stirred for 43 hours. The reaction mixture was treated with water (200 mL) and then extracted with dichloromethane (3×80 mL). The combined extracts were washed with water (3×100 mL), dried over magnesium sulfate, and the solvent subsequently evaporated under vacuum, yielding 17 g of 1-(5-hexenyl)-3,7-dimethylxanthine (65 mmol, 98% yield) as a white powder.

To a mixture of 1-(5-hexenyl)-3,7-dimethylxanthine (1.07 g, 4.1 mmol) and N-methylmorpholine-N-oxide (1.44 g, 12.3 mmol) in water (20 mL) and acetone (10 mL) was added 2.5% osmium tetraoxide in t-butanol (6 drops). After stirring for 48 hours, the mixture was treated with 20% aqueous sodium dithionite solution (20 mL). After 2 minutes, the mixture was extracted with 25% ethanol-dichloromethane solution (3×30 mL). The combined extracts were dried over magnesium sulfate and the solvents were evaporated under vacuum, yielding 750 mg 1-(5,6-dihydroxyhexyl)-3,7-dimethylxanthine (2.53 mmol, 62% yield) as a white powder.

To a solution of 1-(5,6-dihydroxyhexyl)-3,7-dimethylxanthine (0.50 g, 1.56 mmol, prepared above) in dimethylformamide (5 mL) were added p-toluenesulphonic acid (0.005 g) and 2,2-dimethoxypropane (1.0 mL, 8.1 mmol). The resulting reaction mixture was stirred for 24 hours. Water (30 mL) was subsequently added and extracted with ethyl acetate (2×25mL) and the combined organic extracts were washed with water (2×30 mL). The organic phase was dried with anhydrous magnesium sulfate and the solvent evaporated, producing a residue which was then purified by flash chromatography over silica gel using 3% methanol/dichloromethane eluant. 0.31 g of compound no. 1591 was obtained (55% yield).

EXAMPLE 5

This example illustrates the effect of inventive compound no. 1567 as an immune modulator. FIG. 1 shows a mixed lymphocyte reaction of comparative compound no. 1540 (racemate N-(2,3-dihydroxypropyl) theobromine) and inventive compound no.1567. The mixed lymphocyte reaction shows a proliferative response of PBMC (peripheral blood mononuclear cells) to allogeneic stimulation determined in a two-way mixed lymphocyte reaction. Inventive compound no. 1567, but not comparative compound no. 1540, showed activity in this immune modulating activity assay procedure.

EXAMPLE 6

Figure 2:
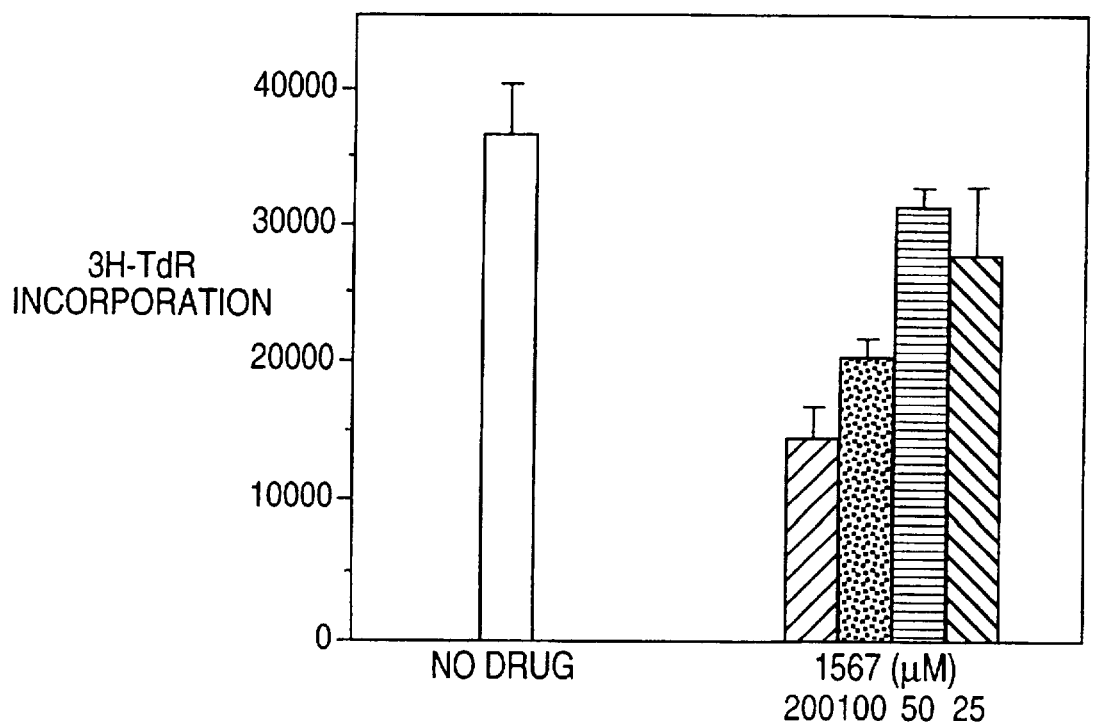
FIG. 2 shows the effects of inventive compound no. 1567 on inhibition of thymocyte proliferation stimulated by Concanavalin A (ConA) and interleukin-1 alpha (IL-1α).

This example illustrates the effects of inventive compound no. 1567 on inhibition of thymocyte proliferation stimulated by ConA (0.25 µg/ml) and IL-1α (12.5 ng/ml). Thymuses were obtained from normal, female Balb/C mice, dissociated, and plated into 96-well plates at a density of 2×10$^5$ cells/well. ConA and IL-Iα were added to the wells and the cells incubated for 4 days at 37° C. On day 4, the cells were pulsed with tritiated thymidine and allowed to incubate for an additional 4 hours. The cells were harvested and incorporated tritiated thymidine was determined in a liquid scintillation counter. Drug was added at the doses indicated two hours prior to activation with ConA and IL-1α. Compound no. 1567 inhibited thymocyte proliferation in a dose-response manner as shown in FIG. 2. Background counts were less than 200 cpm.

EXAMPLE 7

Figure 3:
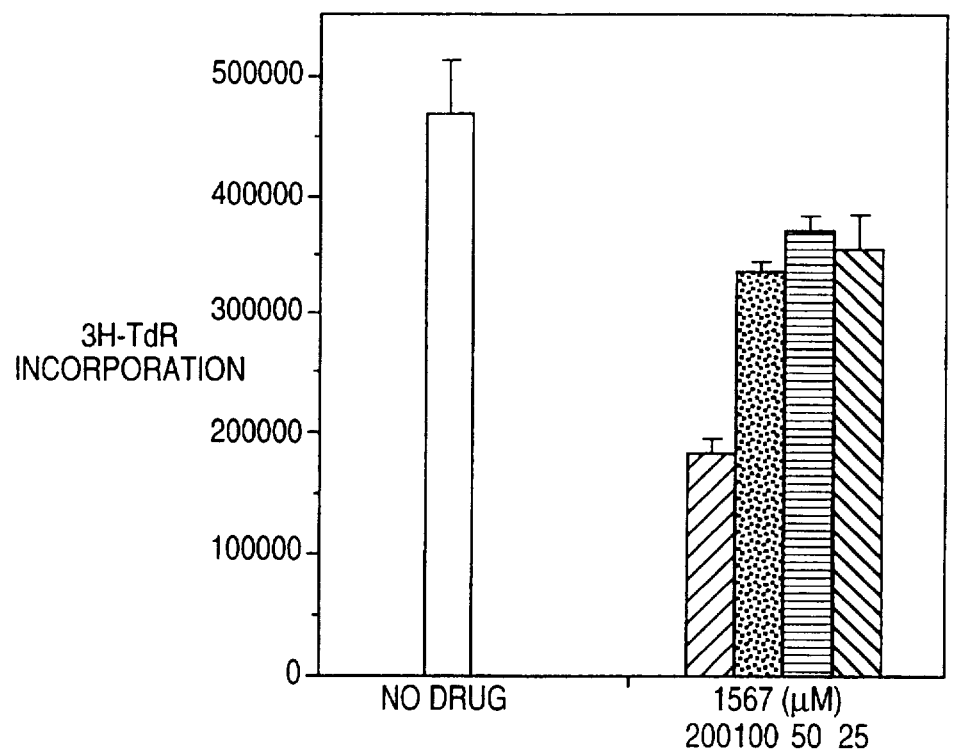
FIG. 3 shows the effects of inventive compound no. 1567 on inhibition of thymocyte proliferation stimulated by ConA and interleukin-1 (IL-2).

This example illustrates the effects of inventive compound no. 1567 on inhibition of thymocyte proliferation stimulated by ConA and IL-2 (20 ng/ml). The procedure described in example 6 was followed, except for addition of IL-2 instead of IL-1 (x. Compound no. 1567 was added to the cells two hours prior to activation with ConA and IL-2. Compound 1567 inhibited thymocyte proliferation at the highest dose tested as shown in FIG. 3.

EXAMPLE 8

Figure 4:
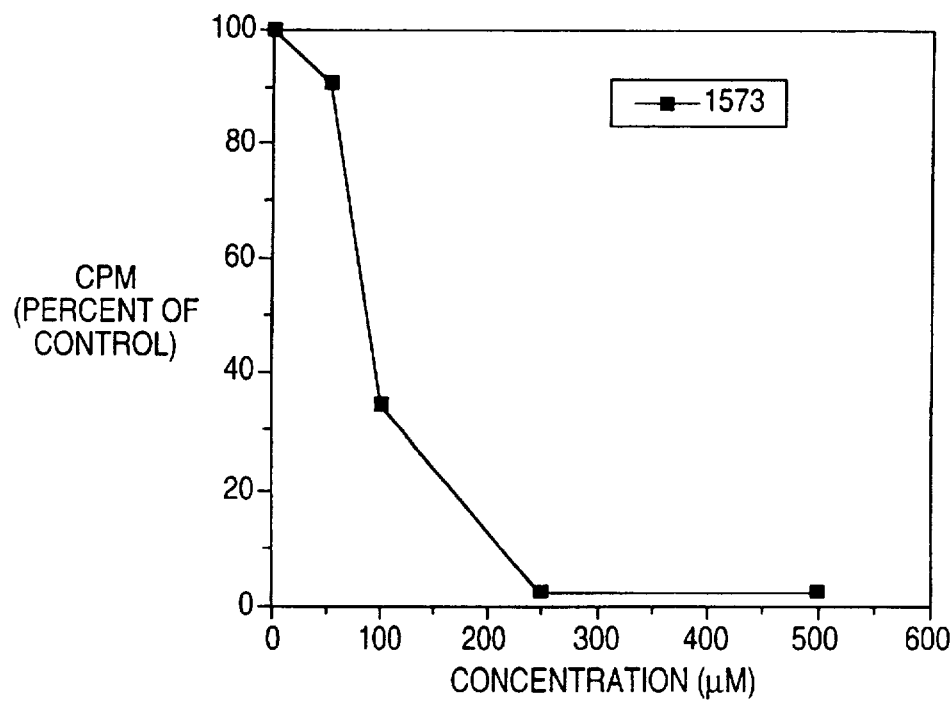
FIG. 4 illustrates the ability of inventive compound no. 1573 to strongly inhibit proliferation of human stromal cells stimulated with PDGF. This assay is a model for restenosis and treatment of atherosclerosis and coronary artery disease.

This example illustrates the ability of inventive compound no. 1573 to strongly inhibit proliferation of human stromal cells when stimulated with PDGF. This assay is a model for restenosis and treatment of atherosclerosis and coronary artery disease. Stromal cells were starved in serum-free media for 24 hours and then stimulated with PDGF-BB (50 ng/ml). The drugs were added at various concentrations one hour prior to PDGF stimulation. Tritiated thymidine was added for 24 hours at the time of PDGF stimulation and proliferation determined by harvesting and counting the cells by liquid scintillation 24 hours later. Background counts (i.e., starved cells) were approximately 1% of control levels. As can be seen from FIG. 4, an IC50 for compound no. 1573 to inhibit stromal cell proliferation stimulated by PDGF BB was less than 100 µM. This concentration is readily achievable in vivo in patients.

EXAMPLE 9

Figure 5:
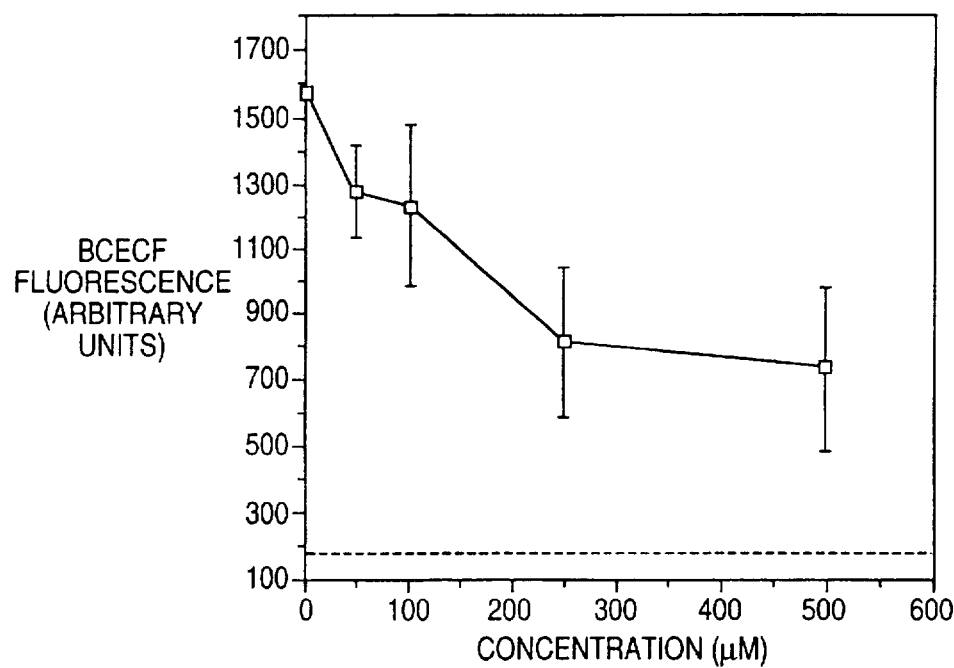
FIG. 5 shows the effect of inventive compound no. 1573 to inhibit adhesion of U937 cells to activated human umbilical vein endothelial cells (HUVEC).

This example illustrates the inhibitive effects of inventive compound no. 1573 on adhesion of U937 cells to activated human umbilical vein endothelial cells (HUVEC). HUVEC cells (4000/well, seeded 72 hours in advance) were activated with 20 ng/ml of human TNF for 12 hours. Inventive compound no. 1573 was added to the samples one hour prior to adding TNF. U937 cells, preloaded with a fluorescent dye (BCECF), were added to the HUVEC cells in each well for 30 minutes, after which time the cells were washed twice with PBS and then adhesion measurements taken. Adhesion was measured on a fluorescence plate reader. Inventive compound no. 1573 reduced adhesion in a dose-dependent manner as shown in FIG. 5. Background adhesion of U937 cells to non-activated HUVEC is shown as a dashed line.

EXAMPLE 10

Figure 6:
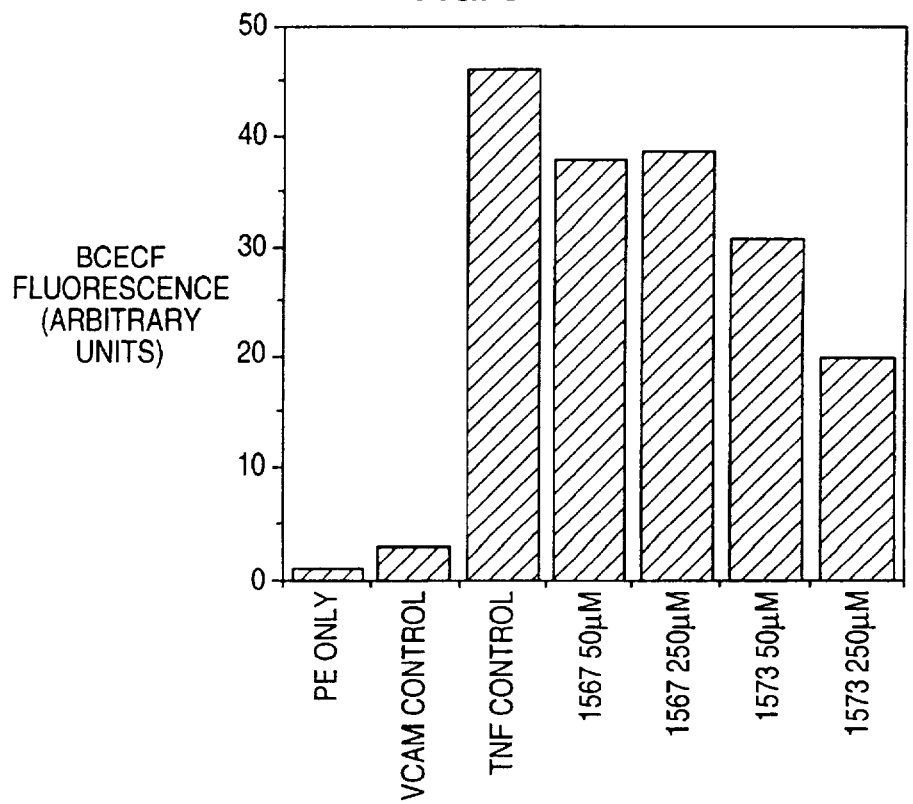
FIG. 6 shows the effects of inventive compounds nos. 1567 and 1573 to inhibit cell surface expression of VCAM in HUVEC cells.

This example illustrates the inhibitive effects of inventive compounds nos. 1567 and 1573 on cell surface expression of VCAM in HUVEC cells. The cells were stimulated with TNF-α (20 ng/ml) for 20 hours and then stained for immunofluorescence using a monoclonal antibody recognizing VCAM, followed by a goat anti-mouse antibody conjugated to phycoerythrin. The cells were analyzed for antibody binding using flow cytometry. FIG. 6 shows an analysis of mean fluorescence intensity of 10,000 cells analyzed by flow cytometry for compounds nos. 1567 and 1573 at the indicated drug concentrations.

EXAMPLE 11

Figure 7:
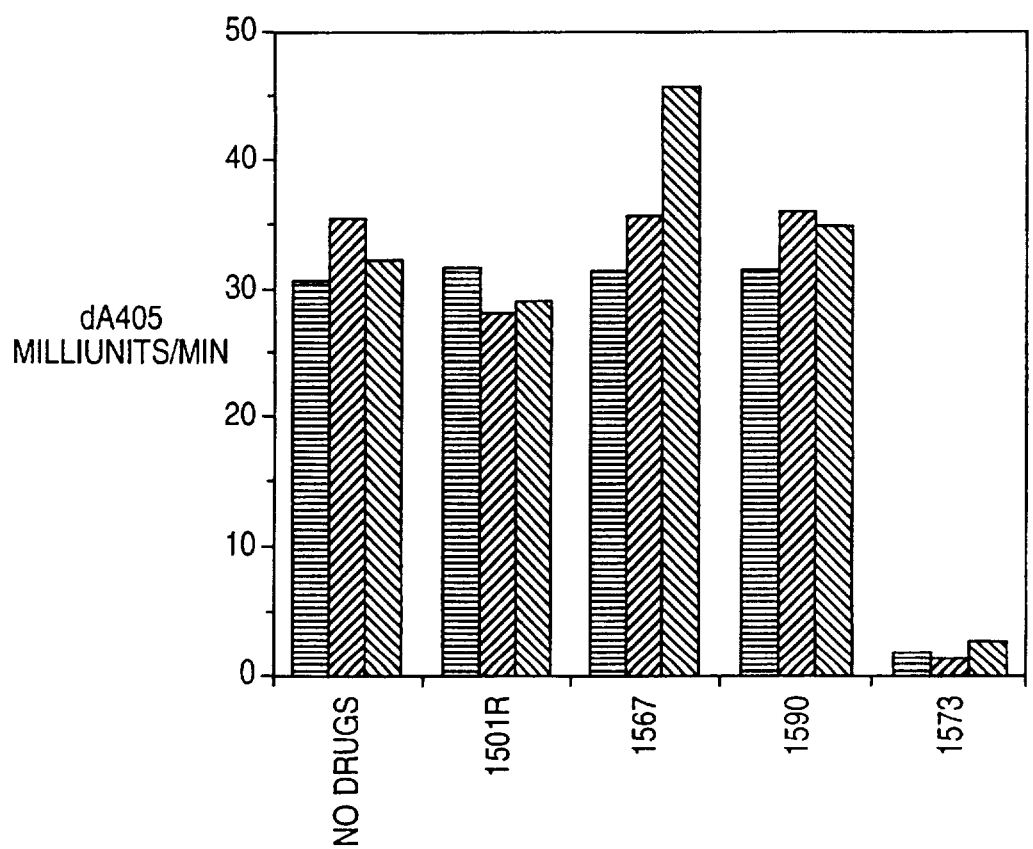
FIG. 7 illustrates the effects of inventive compounds nos. 1590, 1573 and 1567 and compound no. 1501R (an alcohol-substituted xanthine beyond the scope of the invention) on cell proliferation as a measure of antitumor activity and the ability of each drug to inhibit gene expression in tumor cells.

This example illustrates the effects of inventive compounds nos. 1590, 1573 and 1567 and compound no. 1501R (an alcohol-substituted xanthine beyond the scope of the invention) on cell proliferation as a measure of antitumor activity and the ability of each drug to inhibit gene expression in tumor cells. A specific plasmid construct employing a human CMV (cytomegalovirus) promoter directs the expression of a reporter gene (secreted human placental alkaline phosphatase) that was transformed into the tumor cell line 293-EBNA cells. The cells were treated with various concentrations of drug. Antitumor activity was measured in culture supernatants by expression of alkaline phosphatase reporter gene by absorbance at 405 nm of cell conditioned medium in the presence of substrate (e.g., ortho-nitrophenol phosphate) as described in Berger et al. (*Gene* 66:1-10, 1988). FIG. 7 shows that compound no. 1573 strongly inhibited gene expression (i.e., possessed strong antitumor activity) when compared with compound no. 1501R and inventive compounds 1567 and 1590.

EXAMPLE 12

Figure 8:
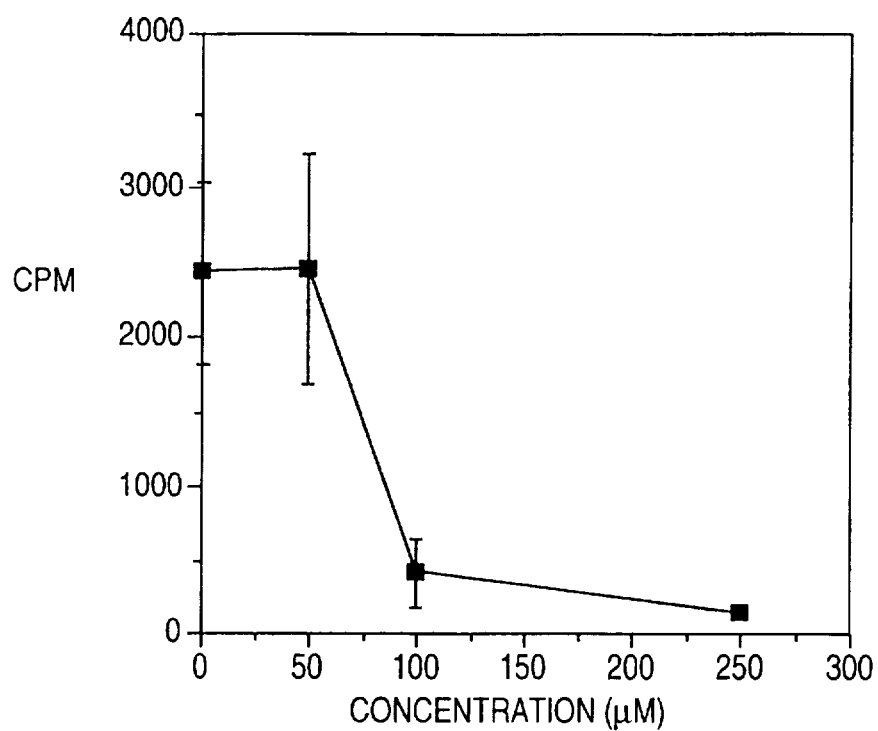
FIG. 8 shows a mixed lymphocyte reaction of inventive compound no. 1590. The mixed lymphocyte reaction shows a proliferative response of PBMC (peripheral blood mononuclear cells) to allogeneic stimulation determined in a two-way mixed lymphocyte reaction.

This example illustrates a mixed lymphocyte reaction (described in example 5 and herein) of inventive compound no. 1590. The mixed lymphocyte reaction shows a proliferative response of PBMC (peripheral blood mononuclear cells) to allogeneic stimulation determined in a two-way mixed lymphocyte reaction. As reported in FIG. 8, compound no. 1590 showed activity in this immune modulating activity assay procedure.

EXAMPLE 13

Figure 9:
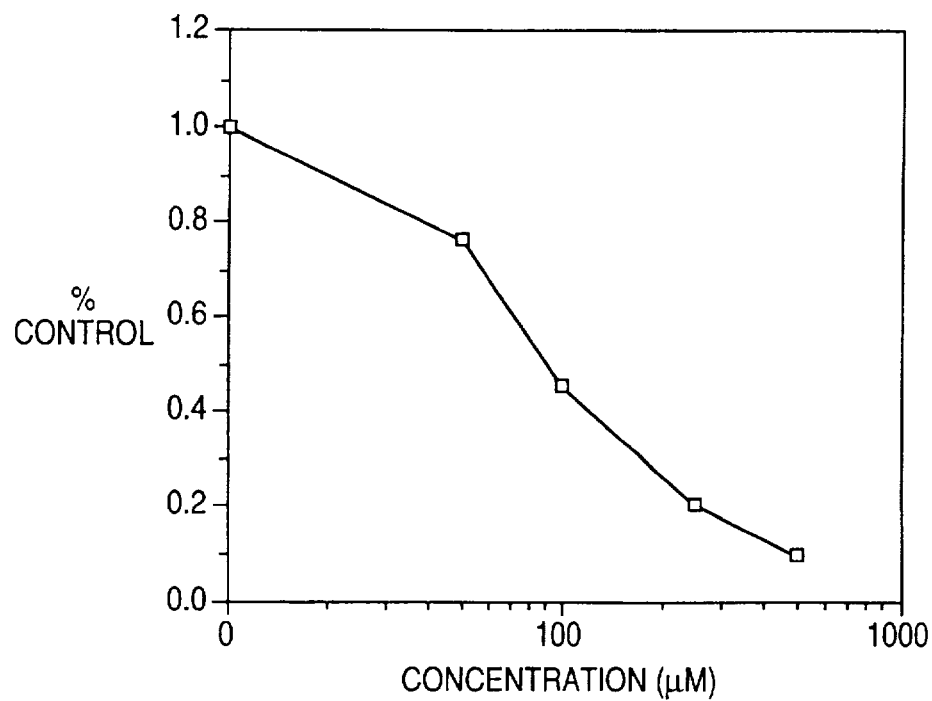
FIG. 9 illustrates the ability of inventive compound no. 1590 to inhibit proliferation of human stromal cells when stimulated with PDGF.

This example illustrates the ability of inventive compound no. 1590 to strongly inhibit proliferation of human stromal cells when stimulated with PDGF. This assay is a model for restenosis and treatment of atherosclerosis and coronary artery disease. The assay is described in example 9 and herein. As illustrated in FIG. 9, an IC50 of compound no. 1590 for inhibiting stromal cell proliferation stimulated by PDGF BB and IL1α0 was about 100 μM. This concentration of drug is readily achievable in vivo in patients.

What is claimed is:

1. A therapeutic compound having the formula:

CORE MOIETY—(R)$_j$, including resolved enantiomers, diastereomers, hydrates, salts, and solvates, wherein:

j is an integer from one to three;

the core moiety is pyrimidinyl;

R is selected from the group consisting of hydrogen, halogen, hydroxyl, amino, $C_{(1-6)}$ alkyl, $C_{(2-6)}$ alkenyl, and formula I, with the proviso that the halogen cannot be bound to the nitrogen atom of the core moiety; and at least one R has a structure according to the following formula I $$—(CH_2)_n—C—(R_1)_3 \qquad I$$

wherein:

n is an integer from five to twenty;

$R_1$ is selected from the group consisting of hydrogen, halogen, hydroxide, $C_{(1-6)}$ alkyl, $C_{(1-6)}$ alkoxyl, $C_{(2-6)}$ alkenyl, or —$OR_2$, $R_2$ being hydrogen, $C_{(1-6)}$ alkyl, $C_{(2-6)}$ alkenyl or —$(CH_2)_p$—$C(R_3)_3$, p being zero or an integer from one to ten, $R_3$ being hydrogen, halogen, hydroxide, $C_{(1-6)}$ alkyl, $C_{(1-6)}$ alkoxyl, $C_{(2-6)}$ alkenyl, or —$OR_2$, $R_2$ being defined above;

at least two $R_1$ or two $R_3$ are —$OR_2$ or jointly form —$(CH_2)_s$—O—C$(R_4)_2$—O—$(CH_2)$t, s and t independently being zero, one or two, a sum of s and t being less than three, and $R_4$ being selected from the group consisting of hydrogen, halogen, $C_{(1-6)}$ alkyl, or $C_{(2-6)}$ alkenyl;

no more than one $R_2$, corresponding to the at least two $R_1$ or two $R_3$ which are —$OR_2$ is hydrogen; and a third $R_1$ or third $R_3$, bonded to the same —C as the at least two $R_1$ or two $R_3$, is other than —$OR_2$.

2. The compound according to claim 1, wherein two terminal $R_2$ of —$C(OR_2)_2$ join, forming a ring having from four to seven atoms, wherein the O of each —$OR_2$ is a member of the ring.

3. The compound according to claim 1, wherein at least one of $(CH_2)_n$ or $(CH_2)_p$ has one or two unsaturated bonds.

4. The compound according to claim 1, wherein n is an integer from about five to about eighteen.

5. The compound according to claim 1, wherein n is an integer from about five to about seven.

6. The compound according to claim 1, wherein $R_1$ of —$C(R_1)_2$ are both —$OR_2$, the two $R_2$ joining to form a ring having five atoms, the —C and each O of the —$C(OR_2)_2$ comprising three of the five ring atoms; or wherein $R_1$ of —$C(R_1)_2$ jointly form —$(CH_2)_s$—O—C $(R_4)_2$—O—$(CH_2)$$_r$, s being one, t being zero and one or both of $R_4$ being hydrogen or unsubstituted $C_{(1-6)}$ alkyl.

7. The compound according to claim 1, wherein when R, $R_1$, $R_2$, $R_3$ or $R_4$ is a substituted $C_{(1-6)}$ alkyl, $C_{(1-6)}$ alkoxy, $C_{(2-6)}$ alkenyl, cyclic or heterocyclic group, a substituent thereon is selected from the group consisting of amide, primary, secondary and tertiary amine, $C_{(2-8)}$ alkenyl, $C_{(1-8)}$ alkyl, $C_{(1-8)}$ alkoxy, azide, carbonate, carbonyl, carboxylic acid, cyanide, $C_{(1-8)}$, haloalkyl, isocyanate, isothiocyanate, phosphate, phosphonate, primary, secondary or tertiary alcohol, sulfonate, sulfone, sulfoxide, thioamide, thiocarbonate, thioester, thiolester, thiol, thiourea and urea.

8. The compound according to claim 7, wherein the alcohol is methanol, butanol, 1-cyclopentanol, ethanol, 2-ethyl-3-methyl-1-propanol, pentanol, propanol or methylcyclohexanol.

9. The compound according to claim 7, wherein the haloalkyl is a mono-, di- or tri-haloalkyl.

10. The compound according to claim 1, wherein the are core moriety is selected from the group consisting of substituted or unsubstituted barbituric acid; thymine; and uracil.

11. The compound according to claim 1, wherein the core moiety is selected from the group consisting of a substituted or unsubstituted methylthymine, methyluracil, thymine, and uracil.

12. The compound according to claim 1, wherein R is bonded to a nitrogen of the core moiety.

13. A pharmaceutical composition comprising a compound of claim 1 in admixture with a pharmaceutically acceptable excipient or carrier.

* * * * *